US011951197B2

(12) United States Patent
Pfister et al.

(10) Patent No.: US 11,951,197 B2
(45) Date of Patent: Apr. 9, 2024

(54) USE OF VOLATILE COMPOUNDS TO MODULATE THE PERCEPTION OF FLORAL MUGUET

(71) Applicant: FIRMENICH SA, Satigny (CH)

(72) Inventors: Patrick Pfister, Plainsboro, NJ (US); Christie Delaura, Plainsboro, NJ (US); Casey Trimmer, Plainsboro, NJ (US); Lily Wu, Plainsboro, NJ (US); Aleksey Dumer, Plainsboro, NJ (US); Florian De Nanteuil, Satigny (CH)

(73) Assignee: FIRMENICH SA, Satigny (CH)

( * ) Notice: Subject to any disclaimer, the term of this patent is extended or adjusted under 35 U.S.C. 154(b) by 180 days.

(21) Appl. No.: 17/294,655

(22) PCT Filed: Dec. 17, 2019

(86) PCT No.: PCT/EP2019/085729
§ 371 (c)(1),
(2) Date: May 17, 2021

(87) PCT Pub. No.: WO2020/127325
PCT Pub. Date: Jun. 25, 2020

(65) Prior Publication Data
US 2022/0008302 A1 Jan. 13, 2022

Related U.S. Application Data

(60) Provisional application No. 62/781,796, filed on Dec. 19, 2018.

(30) Foreign Application Priority Data

Feb. 14, 2019 (EP) ..................................... 19157073

(51) Int. Cl.
*A61K 8/33* (2006.01)
*A61Q 13/00* (2006.01)

(52) U.S. Cl.
CPC ................ *A61K 8/33* (2013.01); *A61Q 13/00* (2013.01)

(58) Field of Classification Search
CPC ....................................................... A61K 8/33
See application file for complete search history.

(56) References Cited

U.S. PATENT DOCUMENTS 3,896,180 A    7/1975  Lemberg
4,081,483 A *  3/1978  Hall ...................... C07C 403/02
                                                426/534

(Continued)

FOREIGN PATENT DOCUMENTS

EP      2100589 A1    9/2009
JP    2017500861 A    1/2017

(Continued)

OTHER PUBLICATIONS

International Search Report and Written Opinion for corresponding PCT/EP2019/085729 dated Jul. 21, 2020, 26 pages.

(Continued)

*Primary Examiner* — Arrie L Reuther

(57) ABSTRACT

Described herein are compositions and/or ingredients that increase a subject's perception of floral muguet compounds, methods for intensifying a subject's perception of floral muguet compounds, as well as perfumed articles or perfuming compositions including as an active ingredient, at least one compound selected from octanal; (E)-dec-2-enal, 2-phenylpropanal; (E)-but-2-enal; 3-methylbenzaldehyde; 3-(1,3-benzodioxol-5-yl)-2-methylpropanal; (±)-3-(4-methyl-3-penten-1-yl)-3-cyclohexene-1-carbaldehyde, (±)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-

(Continued)

dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

16 Claims, 9 Drawing Sheets

(56) References Cited

U.S. PATENT DOCUMENTS

| | | | |
|---|---|---|---|
| 5,952,292 | A | 9/1999 | Snowden et al. |
| 5,990,076 | A | 11/1999 | Gaudin et al. |
| 2010/0130624 | A1 | 5/2010 | Oertling |
| 2013/0336910 | A1 | 12/2013 | Chatelain et al. |
| 2015/0057207 | A1* | 2/2015 | Amorelli ............ C11B 9/0015 568/375 |
| 2015/0110731 | A1 | 4/2015 | Namba et al. |

FOREIGN PATENT DOCUMENTS

| | | |
|---|---|---|
| WO | 2013045301 A1 | 4/2013 |
| WO | 2015095062 A2 | 6/2015 |
| WO | 2016201152 A1 | 12/2016 |
| WO | 2017046071 A1 | 3/2017 |
| WO | 2017174827 A1 | 10/2017 |
| WO | 2018091686 A1 | 5/2018 |
| WO | 2018134221 A1 | 7/2018 |

OTHER PUBLICATIONS

Touhara K et al, "Functional identification and reconstitution of an odorant receptor in single olfactory neurons", PNAS, National Academy of Sciences, US, vol. 96, No. 7, Jan. 1, 1999 (Jan. 1, 1999), p. 4040-4045.

Fukuda Nanaho et al, "Functional characterization of a mouse testicular olfactory receptor and its role in chemosensing and in regulation of sperm motility", Journal of Cell Science,, vol. 117, No. 24, Nov. 15, 2004 (Nov. 15, 2004), p. 5835-5845.

Lamboley et al., "Synthesis and Properties of Conformationally Constrained Analogues of Floral-Type Oderants". Helvetica Chimica Acta, vol. 87, 2004.

* cited by examiner

USE OF VOLATILE COMPOUNDS TO MODULATE THE PERCEPTION OF FLORAL MUGUET

CROSS-REFERENCE TO RELATED APPLICATIONS

This application is a U.S. National Phase Application of International Patent Application No. PCT/EP2019/085729, filed Dec. 17, 2019, which claims the benefit of priority to U.S. Provisional Patent Application No. 62/781,796, filed Dec. 19, 2018, and which claims priority to European Patent Application No. 19157073.8, filed Feb. 14, 2019, the entire contents of which are hereby incorporated by reference herein.

The various aspects presented herein relate to the perfumery industry. More particularly, the various aspects presented herein relate to compositions and/or ingredients that increase a subject's perception of floral muguet compounds, methods for intensifying a subject's perception of floral muguet compounds, as well as to the perfumed articles or perfuming compositions comprising as an active ingredient, at least one compound selected from octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

BACKGROUND

Floral muguet compounds span chemically diverse families of molecules that generate a scent that is highly appreciated in perfumery.

The intensity of the floral muguet scent perceived by a subject is dependent on several factors, such as, but not limited to, the concentration of the floral muguet compound in the perfumed article or perfuming composition, the subject's ability to perceive the floral muguet scent, the efficacy and the affinity to the floral muguet compound for floral muguet olfactory receptors, the particular floral muguet olfactory receptors present in the subject, and the like.

Consequently, there is a need to increase a subject's perception of floral muguet compounds, and/or generate perfumed articles or perfuming compositions wherein the perception of floral muguet is conveyed, enhanced, improved or modified.

SUMMARY

One aspect presented herein provides a method,
wherein the method conveys, enhances, improves or modifies an intensity and/or sensitivity of the perception of a floral muguet odor in a subject in need thereof,
wherein the method comprises contacting the subject with at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof,
wherein the subject is contacted with the at least one positive allosteric modulator in an amount sufficient to convey, enhance, improve or modify the intensity and/or sensitivity of the perception of the floral muguet odor in the subject.

In one aspect, the method further comprises contacting the subject with at least one floral muguet compound.

One aspect presented herein provides a method,
wherein the method increases the potency and/or efficacy of at least one floral muguet compound for a floral muguet olfactory receptor in a subject in need thereof,
wherein the method comprises contacting the subject with at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof,
wherein the subject is contacted with the at least one positive allosteric modulator in an amount sufficient to increase the potency and/or efficacy of the at least one floral muguet compound for a floral muguet olfactory receptor in the subject.

In one aspect, the method further comprises contacting the subject with at least one floral muguet compound.

In one aspect, the method is a non-therapeutic method.

In one aspect, the amount sufficient of the at least one positive allosteric modulator increases the potency and/or efficacy for the floral muguet compound for the floral muguet olfactory receptor 2 fold to 30 fold.

In one aspect, the increase in the potency and/or efficacy of the at least one floral muguet compound for the floral muguet olfactory receptor conveys, enhances, improves or modifies an intensity and/or sensitivity of the perception of a floral muguet odor in the subject.

One aspect presented herein provides a method,
wherein the method conveys, enhances, improves or modifies an intensity and/or sensitivity of the perception of a floral muguet odor of a perfuming composition in a subject in need thereof,
wherein the method comprises decreasing the amount of at least one floral muguet olfactory receptor inhibitor in the perfuming composition below an amount effective to decrease the potency and/or efficacy for at least one floral muguet compound for a floral muguet olfactory receptor in the subject, and wherein the at least one muguet olfactory receptor inhibitor is selected from the group consisting of: (−)-(1R,4R,6S,10S)-4,12,12-trimethyl-9-methylene-5-oxatricyclo[8.2.0.0$^{4,6}$]dodecane, trimethyl-13-oxabicyclo-[10.1.0]-trideca-4,8-diene, (+−)-ethyl 3-methyl-2-oxopentanoate, 7-propyl-2H,4H-1,5-benzodioxepin-3-one.

In one aspect, the at least one positive allosteric modulator is incorporated into a perfuming composition.

In one aspect, the perfuming composition further comprises at least one floral muguet compound.

In one aspect, the perfuming composition is incorporated into a consumer product.

In one aspect, the at least one positive allosteric modulator is incorporated into a consumer product.

In one aspect, the consumer product further comprises at least one floral muguet compound.

In one aspect, the floral muguet olfactory receptor is the OR10J5 olfactory receptor In one aspect, the at least one floral muguet compound is 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof.

One aspect presented herein provides at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof, and wherein the at least one positive allosteric modulator is a positive allosteric modulators of a floral muguet olfactory receptor.

One aspect presented herein provides a use of at least one positive allosteric modulator to convey, enhance, improve or modify an intensity and/or sensitivity of the perception of a floral muguet odor of a perfuming composition in a subject in need thereof.

One aspect presented herein provides a use of a perfuming composition comprising at least one positive allosteric modulator to convey, enhance, improve or modify an intensity and/or sensitivity of the perception of a floral muguet odor of a perfuming composition in a subject in need thereof.

One aspect presented herein provides a use of a consumer product comprising at least one positive allosteric modulator to convey, enhance, improve or modify an intensity and/or sensitivity of the perception of a floral muguet odor of a perfuming composition in a subject in need thereof.

One aspect presented herein provides a use of at least one positive allosteric modulator to increase the potency and/or efficacy for at least one floral muguet compound for a floral muguet olfactory receptor in a subject in need thereof.

One aspect presented herein provides a use of a perfuming composition comprising at least one positive allosteric modulator to increase the potency and/or efficacy for at least one floral muguet compound for a floral muguet olfactory receptor in a subject in need thereof.

One aspect presented herein provides a use of a consumer product comprising at least one positive allosteric modulator to increase the potency and/or efficacy for at least one floral muguet compound for a floral muguet olfactory receptor in a subject in need thereof.

In one aspect, the perfuming composition comprises at least one floral muguet compound.

In one aspect, the consumer product comprises at least one floral muguet compound.

In one aspect, the increase in the potency and/or efficacy for the at least one floral muguet compound for the floral muguet olfactory receptor conveys, enhances, improves or modifies an intensity and/or sensitivity of the perception of a floral muguet odor in the subject.

DETAILED DESCRIPTION

Figure 1:
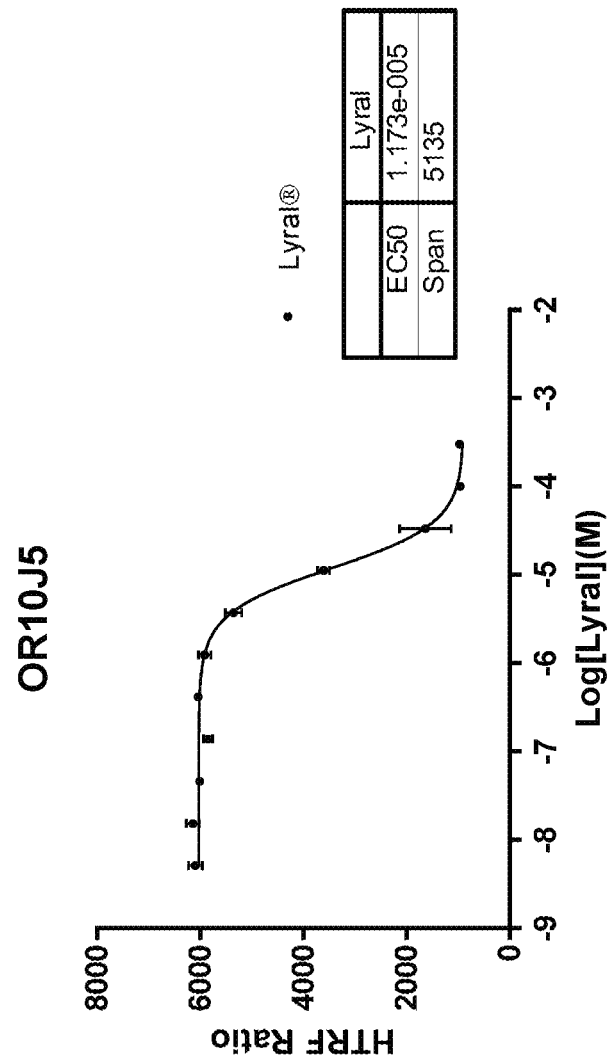
FIG. 1 shows a dose-response curve of OR10J5 to the floral muguet compound 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof (sold under the tradename LYRAL®, hereinafter referred to as "LYRAL®").

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

By the expression, "the method conveys, enhances, improves or modifies an intensity and/or sensitivity of the perception . . . " or similar, it is meant any method having a positive impact on the perception of muguet odor. In other words, the method imparts or modifys in a positive or pleasant way the the perception of a floral muguet odor. According to any aspect of the invention, the method of the invention is a method for enhancing or improving.

Olfactory receptors (OR) are seven-transmembrane members of the large G-protein coupled receptor (GPCR) family and thus exhibit most pharmacological characteristics of the GPCR receptor family. The present disclosure provides volatile compounds that can be used in perfumery applications to modulate, that is, enhance desired fragrances, such as, for example, a floral muguet odor. In some aspects, volatile compounds that enhance the floral muguet odor are positive allosteric modulators of a floral muguet olfactory receptor. Without intending to be limited to any particular theory, synergistic interaction between perfumery ingredients can lead to more sensitive and more intense perception of perfumery tonalities. Such compounds thus enable new routes to optimize perfumery rules and create better performing commercial perfumery formulations.

The ability of compounds of the present disclosure to modulate the activity of a floral muguet olfactory receptor may be determined by any suitable method readily selected by one of ordinary skill in the art, such as, for example, via an ex vivo cultured neuron assay, or via an in vitro assay using a cell line that expresses a floral muguet olfactory receptor.

Such assays for modulators (such as inhibitors and enhancers) and activators include, e.g., expressing OR family members in cells or cell membranes, applying putative modulator compounds, in the presence or absence of agonists, e.g. floral muguet, and then determining the functional effects on olfactory transduction, as described in the Examples below. Samples or assays comprising OR family members that are treated with a potential inhibitor or enhancer are compared to control samples without the inhibitor or the enhancer to examine the extent of inhibition or enhancement. Control samples (untreated with inhibitors or enhancers, but treated with the agonist) are assigned a relative maximal OR activity value of 100%.

Olfactory receptor activity assays may reveal the following data: (i) whether or not a given compound is an activator of the olfactory receptor or not, and the specificity of the compound for the particular olfactory receptor; (ii) the $EC_{50}$ of an agonist for an olfactory receptor (i.e., the $EC_{50}$ of the agonist); and (iii) the efficacy of an agonist for an olfactory receptor, determined by the amplitude of the response (i.e., the span between baseline and saturated activity levels).

In some aspects, enhanced activation of an OR is achieved when the normalized OR activity value (100%) relative to the agonist control is greater than 100%, for example, about 110%, optionally 120% or 150%, or greater. In one aspect, enhancement of an OR is achieved if the potency of an agonist for the OR in the presence of the enhancer compound is increased. In one aspect, the increase in potency is determined via a shift in the $EC_{50}$ for the agonist. Alternatively, in another aspect, enhancement of an OR is achieved if the $EC_{50}$ value of the agonist in the presence of the enhancer compound is decreased from between 2-fold to 30-fold. In one aspect, enhancement of an OR is achieved if the $EC_{50}$ value of the agonist compound is decreased 2-fold. In another aspect, enhancement of an OR is achieved if the $EC_{50}$ value of the agonist in the presence of the enhancer compound is decreased 30-fold.

In some aspects, enhancement of an OR is achieved if the potency and/or efficacy of an OR agonist in the presence of the enhancer compound is increased relative to the agonist control. In one aspect, enhancement of an OR is achieved if the potency and/or efficacy value of the agonist in the presence of the enhancer compound is increased from between 1.05-fold to 2-fold or greater. In one aspect, enhancement of an OR is achieved if the potency and/or efficacy value of the agonist in the presence of the enhancer compound is increased by about 1.05-fold. In another aspect, enhancement of an OR is achieved if the potency and/or efficacy value of the agonist in the presence of the enhancer compound is increased by about 2-fold.

In one aspect, inhibition of an OR is achieved when the normalized OR activity value (100%) relative to the agonist control is less than 100%, for example, about 80%, optionally 50% or 25-0%. In one aspect, inhibition of an OR is achieved if the potency and/or efficacy of an agonist for the OR is decreased. In another aspect, the decrease in potency and/or efficacy is determined via a shift in the $EC_{50}$ for the agonist. In one aspect, inhibition of an OR is achieved if the $EC_{50}$ value of the agonist in the presence of an antagonist compound is increased from between about 2-fold to about 30-fold. In one aspect, inhibition of an OR is achieved if the $EC_{50}$ value of the agonist in the presence of the antagonist compound is increased 2-fold. In one aspect, inhibition of an OR is achieved if the $EC_{50}$ value of the agonist in the presence of the antagonist compound is increased 30-fold.

In some aspects, inhibition of an OR is achieved if the potency and/or efficacy of an OR agonist in the presence of the antagonist compound is decreased. In one aspect, inhibition of an OR is achieved if the potency and/or efficacy value of the agonist in the presence of the antagonist compound is decreased from between about 1.25-fold to 4-fold or greater. In one aspect, inhibition of an OR is achieved if the potency and/or efficacy value of the agonist in the presence of the antagonist compound is decreased to 0. In another aspect, inhibition of an OR is achieved if the potency and/or efficacy value of the agonist in the presence of the antagonist compound is decreased 1.25-fold. In one aspect, inhibition of an OR is achieved if the potency and/or efficacy value of the agonist in the presence of the antagonist compound is decreased 4-fold.

As used herein, the term "olfactory receptor", "odorant receptor", or "OR" refers to one or more members of a family of G protein-coupled receptors (GPCRs) that are expressed in olfactory cells. Olfactory receptor cells can also be identified on the basis of morphology or by the expression of proteins specifically expressed in olfactory cells. OR family members may have the ability to act as receptors for odorants and induce an olfactory transduction cascade.

As used herein, the term "orthosteric binding site" refers to the endogenous agonist (odorant ligands in this case) binding site. A binding event to the orthosteric site generally leads to the activation or the inhibition of the receptor's activity.

As used herein, the term "allosteric binding site" refers to a binding site that is topographically distinct from the orthosteric binding site. Allosteric binding in the presence of orthosteric agonist is not sterically hindered and hence occurs in a non-competing fashion. Certain allosteric ligands can act as either positive allosteric modulators (PAMs) or negative allosteric modulators (NAMs) to potentiate or inhibit activation of the receptor by the endogenous agonist, respectively. Other allosteric binding effects also exist which are not discussed here. Positive or negative allosteric modulators enhance or inhibit the effect of the orthosteric ligand, but are largely inactive in the absence of an orthosteric ligand. Allosteric inhibition or enhancement of a receptor's activity can occur by modulating the receptor's conformation and modify 1) the orthosteric site affinity to its agonists, 2) the effect of orthosteric binding activation (e.g. efficacy) or 3) the binding to the G-protein in the case of GPCRs and decrease or increase the signal transduction efficiency, respectively.

As used herein, the term "cooperativity factor" refers to the degree of modulation of an orthosteric ligand binding effect due to the presence of an allosteric ligand.

In some aspects, the present disclosure presents compounds that inhibit or suppress desired odors, such as, for example, a floral muguet odor. In some aspects, the present disclosure provides perfuming compositions and/or consumer products where compounds that or inhibit or suppress desired odors, such as, for example, a floral muguet odor are reduced or removed, resulting in an enhancement of a subject's perception of a floral muguet odor.

Referring to FIG. 1 and Example 1, olfactory receptor OR10J5 is a human olfactory receptor whose floral muguet compound-induced activity correlates with the sensory outcome of perception of a floral, lily of the valley, hydroxycitronellal odor note, and an overall olfactive character reminding strongly of the one of the very well-known ingredient 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof (sold under the tradename LYRAL®, hereinafter referred to as "LYRAL®".

The OR10J5 olfactory receptor is activated by floral muguet compounds. A floral muguet compound refers to certain compounds that impart a lily of the valley-like or muguet floral note, including but not limited to a lyral compound.

Examples of floral muguet compounds include, but are not limited to the compounds disclosed in International Patent Application Publication Nos. WO2017/009175 A1, or WO2010/091969 A1, or WO2011/029743 A1, or WO2018/134221 A1, or WO2008/068310 A1, or WO2014/198709 A1, or WO2013/117433 A1, or WO2014/180945 A1, or WO2014/180952 A1, or WO2016/074118 A1, or WO2016/074697 A1, or WO2016/074719 A1, WO2014/180952 A1, or WO2001/090038 A1, or WO2008/053148 A1, or WO2017/066214 A1.

Other examples of floral muguet compounds include, but are not limited to the compounds disclosed in U.S. Patent Application Publication Nos. US2013/0090390 A1, or US2011/0117046 A1, or US2011/0118170 A1, or US2009/0036347 A1, or US2011/0217257 A1.

Other examples of floral muguet compounds include, but are not limited to the compounds disclosed in U.S. Pat. No. 5,527,769 A, or 7,834,219 B1, or 2,710,825 A, or 4,352,937 A.

Other examples of floral muguet compounds include, but are not limited to the compounds disclosed in European Patent Application Publication Nos. EP2594626 A1, or EP0392258 A2, or EP2322495 A1, or EP1029845 A1, or EP1054053 A2, or EP1529770 A1.

Other examples of floral muguet compounds include, but are not limited to the compounds disclosed in European Patent Nos. EP2594626 B1, or EP685444 B1, or EP2594626 B1.

Other examples of floral muguet compounds include, but are not limited to the compounds disclosed in UK Patent Application Publication Nos. GB2528467 A, or GB988502 A, or GB1057360 A, or GB2529901 A.

Other examples of floral muguet compounds include, but are not limited to the compounds disclosed in Lamboley et al., Synthesis and Properties of Conformationally Constrained Analogues of Floral-Type Odorants, Helvetica Chimica Acta, vol. 84, pp 1767-1793 (2004).

Other examples of floral muguet compounds include, but are not limited to the compounds disclosed in Schroeder et al., γ-Unsaturated Aldehydes as Potential Lilial Replacers, Chemistry & Biodiversity, vol. 11, pp 1651-1673 (2014.

Other examples of floral muguet compounds include, but are not limited to the compounds disclosed in Skouroumounis et al., Synthesis of 1,3,4,5-Tetrahydro-2-benzoxepin Derivatives as Conformationally Restricted Analogues of Cyclamenaldehyde-Type Compounds and as Intermediates for Highly Odour-Active Homologues, Helvetica Chimica Acta, vol. 79, pp 1095-1109 (1996).

Other examples of floral muguet compounds include, but are not limited to the compounds disclosed in Winter et al., Synthesis and Odor Properties of Substituted Indane-2-carboxaldehydes. Discovery of a New Floral (Muguet) Fragrance Alcohol, Helvetica Chimica Acta, vol. 88, pp 3118-3127 (2005).

Other examples of floral muguet compounds include, but are not limited to the compounds disclosed in Coulomb, J, Beyond Mguet, Perfume and Flavorist, vol. 43 (2018).

In some embodiments, the at least one floral muguet compound is selected from the group consisting of: 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof; 9-hydroxy-5,9-dimethyl-4-decenal; 3-[4-(2-hydroxy-2-methylpropyl)-2-methylphenyl]propanal; 3-[4-(2-hydroxy-2-methylpropyl)phenyl]propanal; (+−)-3-[4-(2-hydroxy-2-methylpropyl)phenyl]-2-methylpropanal; (+−)-4-(4-hydroxy-4-methylpentyl)-3,6-dihydro-2H-pyran-2-carbaldehyde; (2,5-dimethyl-2-indanyl)methyl formate; (2,5-dimethyl-1,3-dihydroinden-2-yl)methanol; (2,5,6-trimethyl-1,3-dihydroinden-2-yl)methanol; (2,4,6-trimethyl-1,3-dihydroinden-2-yl)methanol; 3-[4-(1-hydroxy-2-methyl-2-propanyl)-2-methylphenyl]propanal; 3-[4-(1-hydroxy-2-methyl-2-propanyl)phenyl]propanal; 3-[4-(1-hydroxy-2-methyl-2-propanyl)phenyl]-2-methylpropanal; 3-[4-(2-hydroxyethyl)phenyl]propanal; 3-[4-(1-hydroxy-2-propanyl)phenyl]propanal; 3-[4-(3-hydroxy-2-methyl-2-butanyl)phenyl]propanal; 3-[4-(2-hydroxypropyl)phenyl]propanal; 3-[4-(1-hydroxy-2-methyl-2-propanyl)

phenyl]butanal; 3-{4-[1-(hydroxymethyl)cyclopropyl]phenyl}propanal; 3-[4-(3-hydroxy-2-butanyl)phenyl]propanal; 4-methyl-2-(2-methylpropyl)oxan-4-ol; 7-hydroxy-3,7-dimethyloctanal; and mixtures thereof.

In some embodiments, the at least one floral muguet compound may comprise LYRAL® and/or may comprise a compound such as 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof, which may be sold under the following tradenames: LYRAL®, KOVANOL®, MUGONAL®, and LANDOLAL®.

Positive Allosteric Modulators of the Floral Muguet Olfactory Receptor

Referring to Example 1, the following compounds were found to exhibit potent enhancement of the activity of the OR10J5 olfactory receptor: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; and (E)-non-2-enal.

Accordingly, one aspect presented herein provides at least one positive allosteric modulator selected from the group consisting of:

octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof, and wherein the at least one positive allosteric modulator is a positive allosteric modulator of a floral muguet olfactory receptor.

In one aspect, the positive allosteric modulators specifically enhance the activity of the particular receptor independently of the receptor agonist (activating compound).

In some aspects, the at least one positive allosteric modulator may be modified to prolong, modify, increase, or enhance the olfactive and/or floral muguet enhancement benefit provided the at least one positive allosteric modulator. One example of the modification may be to generate a precursor, or profragrance molecule using the at least one positive allosteric modulator, wherein the profragrance may release any one of the at least one positive allosteric modulators by a chemical reaction during or after application (using $O_2$, light, enzymes, water (pH) or temperature as the release trigger).

In some aspects, the profragrance does not provide any olfactive and/or floral muguet enhancement benefits.

Methods Utilizing Positive Allosteric Modulators of the Floral Muguet Olfactory Receptor According to Some Aspects of the Present Disclosure One aspect presented herein provides a use of at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to convey, enhance, improve or modify an intensity and/or sensitivity of the perception of a floral muguet odor of a perfuming composition in a subject in need thereof. Accordingly, the perfuming composition may comprise at least one floral muguet compound.

According to a particular embodiment, the use of at least one positive allosteric modulator selected from the group consisting of octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to enhance or improve an intensity and/or sensitivity of the perception of a floral muguet odor of a perfuming composition in a subject in need thereof.

One aspect presented herein provides a use of a perfuming composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to convey, enhance, improve or modify an intensity and/or sensitivity of the perception of a floral muguet odor of a perfuming composition in a subject in need thereof.

One aspect presented herein provides a use of a perfuming composition comprising at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to convey, enhance, improve or modify an intensity and/or sensitivity of the perception of a floral muguet odor of a perfuming composition in a subject in need thereof.

One aspect presented herein provides a use of a consumer product comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to convey, enhance, improve or modify an intensity and/or sensitivity of the perception of a floral muguet odor of a perfuming composition in a subject in need thereof.

One aspect presented herein provides a use of a consumer product composition comprising at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to convey, enhance, improve or modify an intensity and/or sensitivity of the perception of a floral muguet odor of a perfuming composition in a subject in need thereof.

In one aspect, the perfume composition is a pre-formulated perfume composition, and the at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof is added to the pre-formulated perfume composition in an amount sufficient to convey, enhance, improve or modify an intensity and/or sensitivity of the perception of a floral muguet odor of a perfuming composition in the subject.

Some aspects presented herein provides a method,
 wherein the method conveys, enhances, improves or modifies an intensity and/or sensitivity of the perception of a floral muguet odor in a subject in need thereof,
 wherein the method comprises contacting the subject with at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof, and
 wherein the subject is contacted with the at least one positive allosteric modulator in an amount sufficient to convey, enhance, improve or modify the intensity and/or sensitivity of the perception of the floral muguet odor in the subject.

In some aspects, the method further comprises contacting the subject with at least one floral muguet compound. The subject may be contacted with the at least one floral muguet compound prior to, simultaneously with, or subsequent to the contacting with the at least one positive allosteric modulator.

Some aspects presented herein provides a method,
 wherein the method conveys, enhances, improves or modifies an intensity and/or sensitivity of the perception of a floral muguet odor in a subject in need thereof,
 wherein the method comprises contacting the subject with a perfuming composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof;

4-ethylbenzaldehyde; 6-methoxy-2,6-dimethylheptanal; (E)-non-2-enal; and combinations thereof, and
wherein the subject is contacted with the at least one positive allosteric modulator in an amount sufficient to convey, enhance, improve or modify the intensity and/or sensitivity of the perception of the floral muguet odor in the subject.

In some aspects, the perfuming composition further comprises at least one floral muguet compound.

Some aspects presented herein provides a method,
wherein the method conveys, enhances, improves or modifies an intensity and/or sensitivity of the perception of a floral muguet odor in a subject in need thereof,
wherein the method comprises contacting the subject with a perfuming composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof, and
wherein the subject is contacted with the at least one positive allosteric modulator in an amount sufficient to convey, enhance, improve or modify the intensity and/or sensitivity of the perception of the floral muguet odor in the subject.

One aspect presented herein provides a use of at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to increase the potency and/or efficacy for at least one floral muguet compound for a floral muguet olfactory receptor in a subject in need thereof.

In some aspects, the increase in potency and/or efficacy for the at least one floral muguet compound for the floral muguet olfactory receptor is determined by a decrease in the $EC_{50}$ for the olfactory receptor activity observed in vitro for the at least one floral muguet compound in the presence of the at least one allosteric modulator, compared to the $EC_{50}$ for the olfactory receptor activity observed in vitro for the at least one floral muguet compound alone.

One aspect presented herein provides a use of a perfuming composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to increase the potency and/or efficacy for at least one floral muguet compound for a floral muguet olfactory receptor in a subject in need thereof.

One aspect presented herein provides a use of a consumer product comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to increase the potency and/or efficacy for at least one floral muguet compound for a floral muguet olfactory receptor in a subject in need thereof.

In some aspects, the perfuming composition comprises at least one floral muguet compound.

In some aspects, the consumer product comprises at least one floral muguet compound.

One aspect presented herein provides a use of a perfuming composition comprising at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to increase the potency and/or efficacy for at least one floral muguet compound for a floral muguet olfactory receptor in a subject in need thereof.

One aspect presented herein provides a use of a consumer product composition comprising at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof to increase the potency and/or efficacy for at least one floral muguet compound for a floral muguet olfactory receptor in a subject in need thereof.

In one aspect, the increase in the potency and/or efficacy for the at least one floral muguet compound for the floral muguet olfactory receptor conveys, enhances, improves or modifies an intensity and/or sensitivity of the perception of a floral muguet odor in the subject.

In one aspect, the perfume composition is a pre-formulated perfume composition, and the at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof is added to the pre-formulated perfume composition in an amount sufficient to increase the potency and/or efficacy for at least one floral muguet compound for a floral muguet olfactory receptor in the subject.

One aspect presented herein provides a method,
wherein the method increases the potency and/or efficacy for at least one floral muguet compound for a floral muguet olfactory receptor in a subject in need thereof,
wherein the method comprises contacting the subject with at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof, and
wherein the subject is contacted with the at least one positive allosteric modulator in an amount sufficient to increase the potency and/or efficacy of the at least one floral muguet compound for a floral muguet olfactory receptor in the subject.

In some aspects, the method further comprises contacting the subject with at least one floral muguet compound. The subject may be contacted with the at least one floral muguet compound prior to, simultaneously with, or subsequent to the contacting with the at least one positive allosteric modulator.

One aspect presented herein provides a method, wherein the method increases the potency and/or efficacy for at least one floral muguet compound for a floral muguet olfactory receptor in a subject in need thereof,
wherein the method comprises contacting the subject with a perfuming composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof, and
wherein the subject is contacted with the at least one positive allosteric modulator in an amount sufficient to increase the potency and/or efficacy of the at least one floral muguet compound for a floral muguet olfactory receptor in the subject.

In some aspects, the perfuming composition further comprises at least one floral muguet compound.

Some aspects presented herein provides a method,
wherein the method conveys, enhances, improves or modifies an intensity and/or sensitivity of the perception of a floral muguet odor in a subject in need thereof,
wherein the method comprises contacting the subject with a perfuming composition comprising at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof, and
wherein the subject is contacted with the at least one positive allosteric modulator in an amount sufficient to increase the potency of the at least one floral muguet compound for a floral muguet olfactory receptor in the subject.

In some aspects, the subject is contacted by treating a surface with, or applying to the subject, or dispensing at least partly in the air, the at least one positive allosteric modulator selected from the group consisting of: octanal; (E)-dec-2- enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

In some aspects, the at least one positive allosteric modulator is incorporated into a perfuming composition.

In some aspects, the perfuming composition further comprises at least one floral muguet compound.

In some aspects, the perfuming composition is incorporated into a consumer product.

In some aspects, the at least one positive allosteric modulator is incorporated into a consumer product.

In some aspects, the consumer product further comprises at least one floral muguet compound.

In some aspects, the floral muguet olfactory receptor is selected from the group consisting of the human OR10J5 olfactory receptor, or the Olfr16 olfactory receptor (the corresponding mouse ortholog). The human olfactory receptor OR10J5 and its corresponding mouse ortholog Olfr16 have approximately 87% sequence identity at the amino acid level.

In some aspects, the amount sufficient of the at least one positive allosteric modulator is from 0.5 to 1000 μM. In some aspects, the amount sufficient of the at least one positive allosteric modulator is from 0.5 to 900 μM. In some aspects, the amount sufficient of the at least one positive allosteric modulator is from 0.5 to 800 μM. In some aspects, the amount sufficient of the at least one positive allosteric modulator is from 0.5 to 700 μM. In some aspects, the amount sufficient of the at least one positive allosteric modulator is from 0.5 to 600 μM. In some aspects, the amount sufficient of the at least one positive allosteric modulator is from 0.5 to 500 μM. In some aspects, the amount sufficient of the at least one positive allosteric modulator is from 0.5 to 400 μM. In some aspects, the amount sufficient of the at least one positive allosteric modulator is from 0.5 to 300 μM. In some aspects, the amount sufficient of the at least one positive allosteric modulator is from 0.5 to 200 μM. In some aspects, the amount sufficient of the at least one positive allosteric modulator is from 0.5 to 100 μM. In some aspects, the amount sufficient of the at least one positive allosteric modulator is from 0.5 to 90 μM. In some aspects, the amount sufficient of the at least one positive allosteric modulator is from 0.5 to 80 μM. In some aspects, the amount sufficient of the at least one positive allosteric modulator is from 0.5 to 70 μM. In some aspects, the amount sufficient of the at least one positive allosteric modulator is from 0.5 to 60 μM. In some aspects, the amount sufficient of the at least one positive allosteric modulator is from 0.5 to 50 μM. In some aspects, the amount sufficient of the at least one positive allosteric modulator is from 0.5 to 40 μM. In some aspects, the amount sufficient of the at least one positive allosteric modulator is from 0.5 to 30 μM. In some aspects, the amount sufficient of the at least one positive allosteric modulator is from 0.5 to 20 μM. In some aspects, the amount sufficient of the at least one positive allosteric modulator is from 0.5 to 10 μM. In some aspects, the amount sufficient of the at least one positive allosteric modulator is from 0.5 to 9 μM. In some aspects, the amount sufficient of the at least one positive allosteric modulator is from 0.5 to 8 μM. In some aspects, the amount sufficient of the at least one positive allosteric modulator is from 0.5 to 7 μM. In some aspects, the amount sufficient of the at least one positive allosteric modulator is from 0.5 to 6 μM. In some aspects, the amount sufficient of the at least one positive allosteric modulator is from 0.5 to 5 μM. In some aspects, the amount sufficient of the at least one positive allosteric modulator is from 0.5 to 4 μM. In some aspects, the amount sufficient of the at least one positive allosteric modulator is from 0.5 to 3 μM. In some aspects, the amount sufficient of the at least one positive allosteric modulator is from 0.5 to 2 μM. In some aspects, the amount sufficient of the at least one positive allosteric modulator is from 0.5 to 1 μM. In some aspects, the amount sufficient of the at least one positive allosteric modulator is from 0.5 to 0.9 μM. In some aspects, the amount sufficient of the at least one positive allosteric modulator is from 0.5 to 0.8 μM. In some aspects, the amount sufficient of the at least one positive allosteric modulator is from 0.5 to 0.7 μM. In some aspects, the amount sufficient of the at least one positive allosteric modulator is from 0.5 to 0.6 μM.

In some aspects, the amount sufficient of the at least one positive allosteric modulator is from 0.6 to 1000 μM. In some aspects, the amount sufficient of the at least one positive allosteric modulator is from 0.7 to 1000 μM. In some aspects, the amount sufficient of the at least one positive allosteric modulator is from 0.8 to 1000 μM. In some aspects, the amount sufficient of the at least one positive allosteric modulator is from 0.9 to 1000 μM. In some aspects, the amount sufficient of the at least one positive allosteric modulator is from 1 to 1000 μM. In some aspects, the amount sufficient of the at least one positive allosteric modulator is from 2 to 1000 μM. In some aspects, the amount sufficient of the at least one positive allosteric modulator is from 3 to 1000 μM. In some aspects, the amount sufficient of the at least one positive allosteric modulator is from 4 to 1000 μM. In some aspects, the amount sufficient of the at least one positive allosteric modulator is from 5 to 1000 μM. In some aspects, the amount sufficient of the at least one positive allosteric modulator is from 6 to 1000 μM. In some aspects, the amount sufficient of the at least one positive allosteric modulator is from 7 to 1000 μM. In some aspects, the amount sufficient of the at least one positive allosteric modulator is from 8 to 1000 μM. In some aspects, the amount sufficient of the at least one positive allosteric modulator is from 9 to 1000 μM. In some aspects, the amount sufficient of the at least one positive allosteric modulator is from 10 to 1000 μM. In some aspects, the amount sufficient of the at least one positive allosteric modulator is from 20 to 1000 μM. In some aspects, the amount sufficient of the at least one positive allosteric modulator is from 30 to 1000 μM. In some aspects, the amount sufficient of the at least one positive allosteric modulator is from 40 to 1000 μM. In some aspects, the amount sufficient of the at least one positive allosteric modulator is from 50 to 1000 μM. In some aspects, the amount sufficient of the at least one positive allosteric modulator is from 60 to 1000 μM. In some aspects, the amount sufficient of the at least one positive allosteric modulator is from 70 to 1000 μM. In some aspects, the amount sufficient of the at least one positive allosteric modulator is from 80 to 1000 μM. In some aspects, the amount sufficient of the at least one positive allosteric modulator is from 90 to 1000 µM. In some aspects, the amount sufficient of the at least one positive allosteric modulator is from 100 to 1000 µM. In some aspects, the amount sufficient of the at least one positive allosteric modulator is from 200 to 1000 µM. In some aspects, the amount sufficient of the at least one positive allosteric modulator is from 300 to 1000 µM. In some aspects, the amount sufficient of the at least one positive allosteric modulator is from 400 to 1000 µM. In some aspects, the amount sufficient of the at least one positive allosteric modulator is from 500 to 1000 µM. In some aspects, the amount sufficient of the at least one positive allosteric modulator is from 600 to 1000 µM. In some aspects, the amount sufficient of the at least one positive allosteric modulator is from 700 to 1000 µM. In some aspects, the amount sufficient of the at least one positive allosteric modulator is from 800 to 1000 µM. In some aspects, the amount sufficient of the at least one positive allosteric modulator is from 900 to 1000 µM.

In some aspects, the amount sufficient of the at least one positive allosteric modulator is from 0.5, or 0.6, or 0.7, or 0.8, or 0.9, or 1, or 2, or 3, or 4, or 5, or 6, or 7, or 8, or 9, or 10, or 20, or 30, or 40, or 50, or 60, or 70, or 80, or 90, or 100, or 200, or 300, or 400, or 500, or 600, or 700, or 800, or 900, or 1000 µM.

In some aspects, the amount sufficient of the at least one positive allosteric modulator increases the potency and/or efficacy for the at least one floral muguet compound for a floral muguet olfactory receptor 2 fold to 100 fold. In some aspects, the amount sufficient of the at least one positive allosteric modulator increases the potency and/or efficacy for the at least one floral muguet compound for a floral muguet olfactory receptor 2 fold to 90 fold. In some aspects, the amount sufficient of the at least one positive allosteric modulator increases the potency and/or efficacy for the at least one floral muguet compound for a floral muguet olfactory receptor 2 fold to 80 fold. In some aspects, the amount sufficient of the at least one positive allosteric modulator increases the potency and/or efficacy for the at least one floral muguet compound for a floral muguet olfactory receptor 2 fold to 70 fold. In some aspects, the amount sufficient of the at least one positive allosteric modulator increases the potency and/or efficacy for the at least one floral muguet compound for a floral muguet olfactory receptor 2 fold to 60 fold. In some aspects, the amount sufficient of the at least one positive allosteric modulator increases the potency and/or efficacy for the at least one floral muguet compound for a floral muguet olfactory receptor 2 fold to 50 fold. In some aspects, the amount sufficient of the at least one positive allosteric modulator increases the potency and/or efficacy for the at least one floral muguet compound for a floral muguet olfactory receptor 2 fold to 40 fold. In some aspects, the amount sufficient of the at least one positive allosteric modulator increases the potency and/or efficacy for the at least one floral muguet compound for a floral muguet olfactory receptor 2 fold to 30 fold. In some aspects, the amount sufficient of the at least one positive allosteric modulator increases the potency and/or efficacy for the at least one floral muguet compound for a floral muguet olfactory receptor 2 fold to 20 fold. In some aspects, the amount sufficient of the at least one positive allosteric modulator increases the potency and/or efficacy for the at least one floral muguet compound for a floral muguet olfactory receptor 2 fold to 19 fold. In some aspects, the amount sufficient of the at least one positive allosteric modulator increases the potency and/or efficacy for the at least one floral muguet compound for a floral muguet olfactory receptor 2 fold to 18 fold. In some aspects, the amount sufficient of the at least one positive allosteric modulator increases the potency and/or efficacy for the at least one floral muguet compound for a floral muguet olfactory receptor 2 fold to 17 fold. In some aspects, the amount sufficient of the at least one positive allosteric modulator increases the potency and/or efficacy for the at least one floral muguet compound for a floral muguet olfactory receptor 2 fold to 16 fold. In some aspects, the amount sufficient of the at least one positive allosteric modulator increases the potency and/or efficacy for the at least one floral muguet compound for a floral muguet olfactory receptor 2 fold to 15 fold. In some aspects, the amount sufficient of the at least one positive allosteric modulator increases the potency and/or efficacy for the at least one floral muguet compound for a floral muguet olfactory receptor 2 fold to 14 fold. In some aspects, the amount sufficient of the at least one positive allosteric modulator increases the potency and/or efficacy for the at least one floral muguet compound for a floral muguet olfactory receptor 2 fold to 13 fold. In some aspects, the amount sufficient of the at least one positive allosteric modulator increases the potency and/or efficacy for the at least one floral muguet compound for a floral muguet olfactory receptor 2 fold to 12 fold. In some aspects, the amount sufficient of the at least one positive allosteric modulator increases the potency and/or efficacy for the at least one floral muguet compound for a floral muguet olfactory receptor 2 fold to 11 fold. In some aspects, the amount sufficient of the at least one positive allosteric modulator increases the potency and/or efficacy for the at least one floral muguet compound for a floral muguet olfactory receptor 2 fold to 10 fold. In some aspects, the amount sufficient of the at least one positive allosteric modulator increases the potency and/or efficacy for the at least one floral muguet compound for a floral muguet olfactory receptor 2 fold to 9 fold. In some aspects, the amount sufficient of the at least one positive allosteric modulator increases the potency and/or efficacy for the at least one floral muguet compound for a floral muguet olfactory receptor 2 fold to 8 fold. In some aspects, the amount sufficient of the at least one positive allosteric modulator increases the potency and/or efficacy for the at least one floral muguet compound for a floral muguet olfactory receptor 2 fold to 7 fold. In some aspects, the amount sufficient of the at least one positive allosteric modulator increases the potency and/or efficacy for the at least one floral muguet compound for a floral muguet olfactory receptor 2 fold to 6 fold. In some aspects, the amount sufficient of the at least one positive allosteric modulator increases the potency and/or efficacy for the at least one floral muguet compound for a floral muguet olfactory receptor 2 fold to 5 fold. In some aspects, the amount sufficient of the at least one positive allosteric modulator increases the potency and/or efficacy for the at least one floral muguet compound for a floral muguet olfactory receptor 2 fold to 4 fold. In some aspects, the amount sufficient of the at least one positive allosteric modulator increases the potency and/or efficacy for the at least one floral muguet compound for a floral muguet olfactory receptor 2 fold to 3 fold.

In some aspects, the amount sufficient of the at least one positive allosteric modulator increases the potency and/or efficacy for the at least one floral muguet compound for a floral muguet olfactory receptor 3 fold to 30 fold. In some aspects, the amount sufficient of the at least one positive allosteric modulator increases the potency and/or efficacy for the at least one floral muguet compound for a floral muguet olfactory receptor 4 fold to 30 fold. In some aspects, the amount sufficient of the at least one positive allosteric modulator increases the potency and/or efficacy for the at least one floral muguet compound for a floral muguet olfactory receptor 5 fold to 30 fold. In some aspects, the amount sufficient of the at least one positive allosteric modulator increases the potency and/or efficacy for the at least one floral muguet compound for a floral muguet olfactory receptor 6 fold to 30 fold. In some aspects, the amount sufficient of the at least one positive allosteric modulator increases the potency and/or efficacy for the at least one floral muguet compound for a floral muguet olfactory receptor 7 fold to 30 fold. In some aspects, the amount sufficient of the at least one positive allosteric modulator increases the potency and/or efficacy for the at least one floral muguet compound for a floral muguet olfactory receptor 8 fold to 30 fold. In some aspects, the amount sufficient of the at least one positive allosteric modulator increases the potency and/or efficacy for the at least one floral muguet compound for a floral muguet olfactory receptor 9 fold to 30 fold. In some aspects, the amount sufficient of the at least one positive allosteric modulator increases the potency and/or efficacy for the at least one floral muguet compound for a floral muguet olfactory receptor 10 fold to 30 fold. In some aspects, the amount sufficient of the at least one positive allosteric modulator increases the potency and/or efficacy for the at least one floral muguet compound for a floral muguet olfactory receptor 11 fold to 30 fold. In some aspects, the amount sufficient of the at least one positive allosteric modulator increases the potency and/or efficacy for the at least one floral muguet compound for a floral muguet olfactory receptor 12 fold to 30 fold. In some aspects, the amount sufficient of the at least one positive allosteric modulator increases the potency and/or efficacy for the at least one floral muguet compound for a floral muguet olfactory receptor 13 fold to 30 fold. In some aspects, the amount sufficient of the at least one positive allosteric modulator increases the potency and/or efficacy for the at least one floral muguet compound for a floral muguet olfactory receptor 14 fold to 30 fold. In some aspects, the amount sufficient of the at least one positive allosteric modulator increases the potency and/or efficacy for the at least one floral muguet compound for a floral muguet olfactory receptor 15 fold to 30 fold. In some aspects, the amount sufficient of the at least one positive allosteric modulator increases the potency and/or efficacy for the at least one floral muguet compound for a floral muguet olfactory receptor 16 fold to 30 fold. In some aspects, the amount sufficient of the at least one positive allosteric modulator increases the potency and/or efficacy for the at least one floral muguet compound for a floral muguet olfactory receptor 17 fold to 30 fold. In some aspects, the amount sufficient of the at least one positive allosteric modulator increases the potency and/or efficacy for the at least one floral muguet compound for a floral muguet olfactory receptor 18 fold to 30 fold. In some aspects, the amount sufficient of the at least one positive allosteric modulator increases the potency and/or efficacy for the at least one floral muguet compound for a floral muguet olfactory receptor 19 fold to 30 fold. In some aspects, the amount sufficient of the at least one positive allosteric modulator increases the potency and/or efficacy for the at least one floral muguet compound for a floral muguet olfactory receptor 20 fold to 30 fold. In some aspects, the amount sufficient of the at least one positive allosteric modulator increases the potency and/or efficacy for the at least one floral muguet compound for a floral muguet olfactory receptor 21 fold to 30 fold. In some aspects, the amount sufficient of the at least one positive allosteric modulator increases the potency and/or efficacy for the at least one floral muguet compound for a floral muguet olfactory receptor 22 fold to 30 fold. In some aspects, the amount sufficient of the at least one positive allosteric modulator increases the potency and/or efficacy for the at least one floral muguet compound for a floral muguet olfactory receptor 23 fold to 30 fold. In some aspects, the amount sufficient of the at least one positive allosteric modulator increases the potency and/or efficacy for the at least one floral muguet compound for a floral muguet olfactory receptor 24 fold to 30 fold. In some aspects, the amount sufficient of the at least one positive allosteric modulator increases the potency and/or efficacy for the at least one floral muguet compound for a floral muguet olfactory receptor 25 fold to 30 fold. In some aspects, the amount sufficient of the at least one positive allosteric modulator increases the potency and/or efficacy for the at least one floral muguet compound for a floral muguet olfactory receptor 26 fold to 30 fold. In some aspects, the amount sufficient of the at least one positive allosteric modulator increases the potency and/or efficacy for the at least one floral muguet compound for a floral muguet olfactory receptor 27 fold to 30 fold. In some aspects, the amount sufficient of the at least one positive allosteric modulator increases the potency and/or efficacy for the at least one floral muguet compound for a floral muguet olfactory receptor 28 fold to 30 fold. In some aspects, the amount sufficient of the at least one positive allosteric modulator increases the potency and/or efficacy for the at least one floral muguet compound for a floral muguet olfactory receptor 29 fold to 30 fold.

In some aspects, the amount sufficient of the at least one positive allosteric modulator increases the potency and/or efficacy for the at least one floral muguet compound for a floral muguet olfactory receptor 2, or 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28, or 29, or 30 fold.

Devices and Applications

In some aspects, the time at which the subject's perception of the floral muguet odor is conveyed, enhanced, improved or modified may be controlled by dispensing at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof at a given time. For example, an at least one floral muguet compound may be dispensed at a first time, and the at least one allosteric modulator may be dispensed at a second time.

Accordingly, some aspects presented herein provide a method to convey, enhance, improve or modify an intensity and/or sensitivity of the perception of a floral muguet odor in a subject in need thereof, comprising dispensing sequentially at least partly in the air, at least one floral muguet compound followed by at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Alternatively, some aspects presented herein provide a method to convey, enhance, improve or modify an intensity and/or sensitivity of the perception of a floral muguet odor in a subject in need thereof, comprising contacting sequentially the subject with at least one floral muguet compound followed by at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Some aspects presented herein provide a method to convey, enhance, improve or modify an intensity and/or sensitivity of the perception of a floral muguet odor in a subject in need thereof, comprising contacting the subject simultaneously with at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Some aspects presented herein provide a method to convey, enhance, improve or modify an intensity and/or sensitivity of the perception of a floral muguet odor in a subject in need thereof, comprising dispensing simultaneously at least partly in the air at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Some aspects presented herein provide a method to convey, enhance, improve or modify an intensity and/or sensitivity of the perception of a floral muguet odor in a subject in need thereof, comprising dispensing sequentially at least partly in the air, a perfuming composition comprising at least one floral muguet compound followed by a perfuming composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Alternatively, some aspects presented herein provide a method to convey, enhance, improve or modify an intensity and/or sensitivity of the perception of a floral muguet odor in a subject in need thereof, comprising contacting sequentially the subject with a perfuming composition comprising at least one floral muguet compound followed by a perfuming composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Some aspects presented herein provide a method to convey, enhance, improve or modify an intensity and/or sensitivity of the perception of a floral muguet odor in a subject in need thereof, comprising contacting the subject simultaneously with a perfuming composition comprising at least one positive allosteric modulator selected from the group consisting of: octanal; (E)-dec-2-enal, 2-phenylpropanal;

(E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Some aspects presented herein provide a method to convey, enhance, improve or modify an intensity and/or sensitivity of the perception of a floral muguet odor in a subject in need thereof, comprising dispensing simultaneously at least partly in the air a perfuming composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Accordingly, some aspects presented herein provide a method to increase the potency and/or efficacy for at least one floral muguet compound for a floral muguet olfactory receptor in a subject in need thereof, comprising dispensing sequentially at least partly in the air, at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Alternatively, some aspects presented herein provide a method to increase the potency and/or efficacy for at least one floral muguet compound for a floral muguet olfactory receptor in a subject in need thereof, comprising contacting sequentially the subject with at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Some aspects presented herein provide a method to increase the potency and/or efficacy for at least one floral muguet compound for a floral muguet olfactory receptor in a subject in need thereof, comprising contacting the subject simultaneously with at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Some aspects presented herein provide a method to increase the potency and/or efficacy for at least one floral muguet compound for a floral muguet olfactory receptor in a subject in need thereof, comprising dispensing simultaneously at least partly in the air at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Some aspects presented herein provide a method to increase the potency and/or efficacy for at least one floral muguet compound for a floral muguet olfactory receptor in a subject in need thereof, comprising dispensing sequentially at least partly in the air, a perfuming composition comprising at least one floral muguet compound followed by a perfuming composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof;

4-ethylbenzaldehyde; 6-methoxy-2,6-dimethylheptanal; (E)-non-2-enal; and combinations thereof.

Alternatively, some aspects presented herein provide a method to increase the potency and/or efficacy for at least one floral muguet compound for a floral muguet olfactory receptor in a subject in need thereof, comprising contacting sequentially the subject with a perfuming composition comprising at least one floral muguet compound followed by a perfuming composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Some aspects presented herein provide a method to increase the potency and/or efficacy for at least one floral muguet compound for a floral muguet olfactory receptor in a subject in need thereof, comprising contacting the subject simultaneously with a perfuming composition comprising at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

Some aspects presented herein provide a method to increase the potency and/or efficacy for at least one floral muguet compound for a floral muguet olfactory receptor in a subject in need thereof, comprising dispensing simultaneously at least partly in the air a perfuming composition comprising at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

In some aspects, the sequential dispensing is performed using a device configured to sequentially emanate separate fragrances at timed intervals from each other. Devices suitable for this include the AIRWICK® SYMPHONIA device which is configured to receive two separate bottles of fragrance and sequentially direct heat toward each bottle to accelerate the evaporation of fragrance therefrom. In some aspects, the device configured to sequentially emanate separate fragrances may also emanate a functional composition. Examples of functional compositions include malodor counteracting compositions, insect repellant compositions, and the like.

U.S. Patent Application Publication No. 2013/0156408 A1 discloses an example of a device configured to sequentially emanate separate fragrances at timed intervals from each other.

U.S. Patent Application Publication No. 2013/0156408 A1 discloses an example of methods to sequentially emanate separate fragrances at timed intervals from each other.

U.S. Patent Application Publication No. 2015/0098860 A1 discloses an example of methods to sequentially emanate separate fragrances at timed intervals from each other.

In some aspects, the device comprises dispensing means for dispersing sequentially in the air volatile compositions and a composition as defined in any of the above-described aspects. In some aspects, the device is such that the first accord and the second accord are physically separated by separating means. According to one aspect, the device is an air-freshener. By sequentially diffusing contrasting accords, the intensity of the perfume can be improved over time.

One aspect presented herein provides a manufactured product comprising the perfume composition according to an aspect presented herein. In one aspect, the manufactured product is selected from the group consisting of a perfume, eau de toilette, home care product and a personal care product.

In some aspects, the term "contacting" refers to administering to a subject, a composition as described herein, wherein the administering results in dosing the subject with an effective amount of the at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof. Administration may be via any method readily selected by one of ordinary skill in the art. Methods include, but are not limited to, topical administration, inhalation, and the like. Accordingly the present disclosure contemplates formulating a composition comprising a compound of Formula (I) as described herein with a suitable carrier to facilitate administering the a composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof as described herein to the subject.

Alternatively, in some aspects, the term "contacting" refers to dispensing or dispersing a composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof as described herein into a volume in need thereof, wherein the dispensing or dispersing results in dosing the subject with an effective amount of at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof as described herein may be achieved by any method readily selected by one of ordinary skill in the art. Examples include, but are not limited to, a spray, a nebulizer, evaporation of a solution containing at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof as described herein, and the like.

Accordingly the present disclosure contemplates formulating a composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof as described herein with a suitable carrier to facilitate treating a surface or volume with a composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof as described herein to the subject.

In some aspects, the term "contacting" refers to contacting a surface of a malodor source with a composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof as described herein, wherein the contacting results in an effective amount of the at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof being deposited on the surface. A composition comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof as described herein may be contacted on a surface by any method readily selected by one of ordinary skill in the art. Examples include, but are not limited to, a spray, a wipe, a solution, and the like.

Products and Formulations According to Some Aspects Presented Herein

In some aspects, the present disclosure provides a perfumed consumer product comprising at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof in an amount sufficient to convey, enhance, improve or modify the intensity and/or sensitivity of the perception of the floral muguet odor in the subject. In some aspects, the perfumed consumer product is selected from the group consisting of: air care products, home care products and laundry care products.

In some aspects, the present disclosure provides a perfumed consumer product comprising at least one floral muguet compound and at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof in an amount sufficient to convey, enhance, improve or modify the intensity and/or sensitivity of the perception of the floral muguet odor in the subject. In some aspects, the perfumed consumer product is selected from the group consisting of: air care products, home care products and laundry care products.

In some aspects, the perfumed consumer product may further comprise a decreased level of at least one floral muguet olfactory receptor inhibitor, wherein the amount of the at least one floral muguet olfactory receptor inhibitor in the perfuming composition is below an amount effective to decrease the potency and/or efficacy for the at least one floral muguet compound for a floral muguet olfactory receptor in a subject. In some aspects, the subject's perception of the floral muguet odor of the perfuming composition is conveyed, enhanced, improved or modified.

The terms "antagonists," "inhibitor," "blockers," "suppressors," "counteractants" and "modulators" of olfactory receptors are used interchangeably to refer to inhibitory, blocking, suppressing, or modulating molecules identified using in vivo, ex vivo and in vitro assays for olfactory transduction, e.g., ligands, antagonists, and their homologs and mimetics. Inhibitors are compounds that, e.g., bind to, partially or totally block stimulation, decrease, suppress, prevent, delay activation, inactivate, desensitize, or down regulate olfactory transduction, e.g., antagonists.

Figure 9:
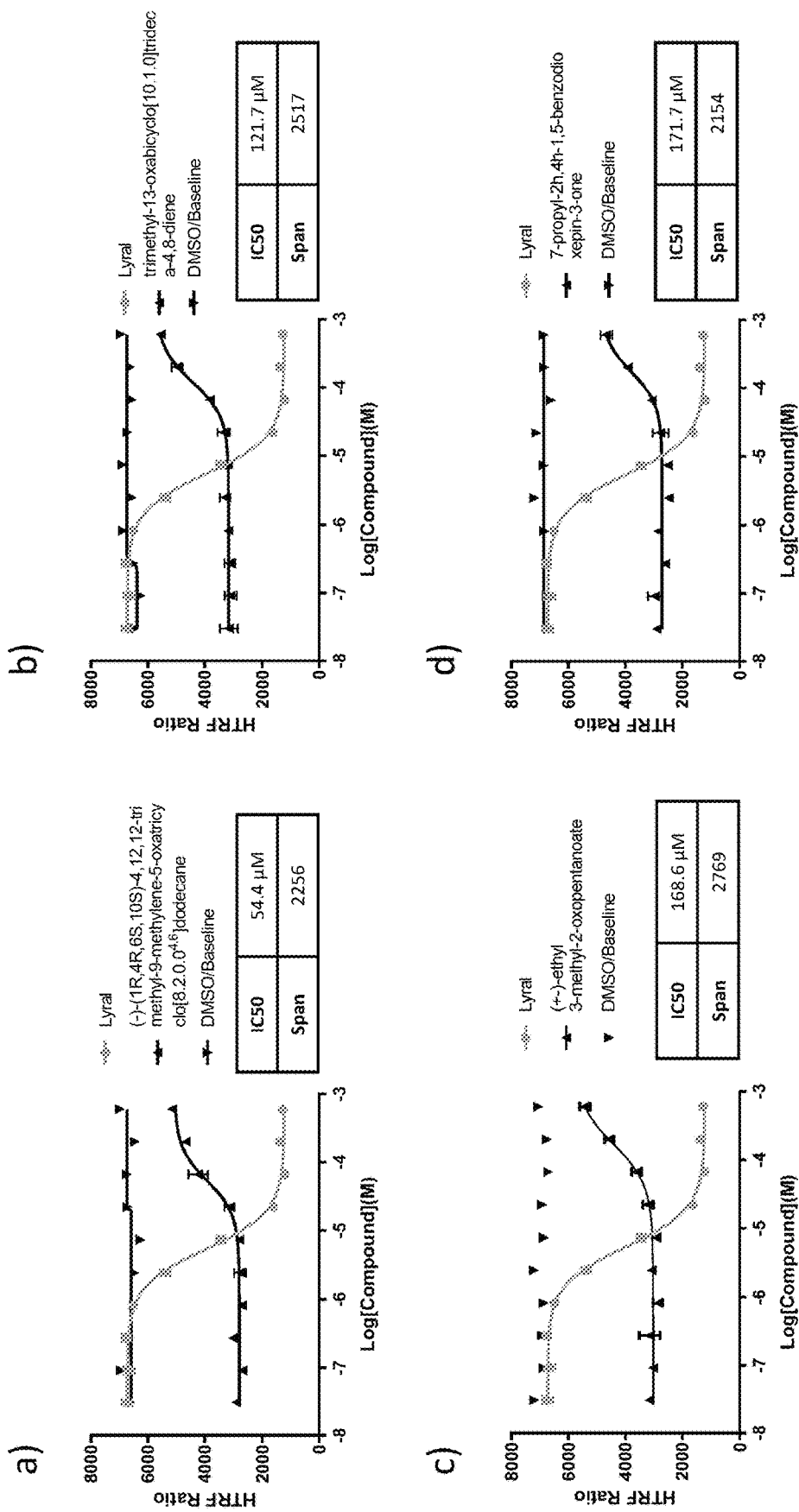
FIG. 9 shows the distinct decreased activity levels obtained on OR10J5 (+−)-2,5-dimethyl-2-indanmethanol-induced activation with a) (−)-(1R,4R,6S,10S)-4,12,12-trimethyl-9-methylene-5-oxatricyclo[8.2.0.0$^{4,6}$]dodecane, b) trimethyl-13-oxabicyclo-[10.1.0]-trideca-4,8-diene, c) (+−)-ethyl 3-methyl-2-oxopentanoate, d) 7-propyl-2H,4H-1,5-benzodioxepin-3-one.

Referring to FIG. 9, the following compounds were found to inhibit the activity of the OR10J5 olfactory receptor: (−)-(1R,4R,6S,10S)-4,12,12-trimethyl-9-methylene-5-oxatricyclo[8.2.0.0$^{4,6}$]dodecane, trimethyl-13-oxabicyclo-[10.1.0]-trideca-4,8-diene, (+−)-ethyl 3-methyl-2-oxopentanoate, 7-propyl-2H,4H-1,5-benzodioxepin-3-one.

It is understood by a person skilled in the art that the at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof, as defined herein, may be added into composition described herein in neat form, or in a solvent. Alternatively, the at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof may first be modified, for example by entrapped with an entrapment material such as for example polymers, capsules, microcapsules, nanocapsules, liposomes, precursors, film formers, absorbents such as for example by using carbon or zeolites, cyclic oligosaccharides and mixtures thereof. Alternatively, the at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof may be chemically bound to substrates which are adapted to release the compounds upon application of an exogenous stimulus such as light, enzymes, or the like.

Accordingly, some aspects presented herein provide a composition comprising:

a. at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof;

b. at least one ingredient selected from the group consisting of a perfumery carrier and a perfumery base; and c. optionally at least one perfumery adjuvant.

Another object of the present invention is a perfuming composition comprising a) one or more compound selected from the group consisting of octanal, (E)-dec-2-enal, 2-phenylpropanal, (E)-but-2-enal, 3-methylbenzaldehyde, 3-(1,3-benzodioxol-5-yl)-2-methylpropanal, (+−)-3-(4-methyl-3-penten-1-yl)-3-cyclohexene-1-carbaldehyde, (+−)-4-(4-methyl-3-penten-1-yl)-3-cyclohexene-1-carbaldehyde, heptanal, 4-Propan-2-ylbenzaldehyde, (3R)-3,7-dimethyloct-6-enal, (+)-(3S)-3-[(1R)-4-methyl-3-cyclohexen-1-yl]butanal, (+)-(3R)-3-[(1R)-4-methyl-3-cyclohexen-1-yl]butanal, hexanal, 2,6-dimethylhept-5-enal, benzaldehyde, 2-methyl-3-(4-methylphenyl)propanal, 3,5,6-trimethyl-3-cyclohexene-1-carbaldehyde, 2,4,6-trimethyl-3-cyclohexene-1-carbaldehyde, 4-ethylbenzaldehyde, 6-methoxy-2,6-dimethylheptanal, (E)-non-2-enal; and b) one or more perfuming ingredient imparting a lily of the valley odor.

According to a particular embodiment, the perfuming composition comprises no lily of the valley olfactory receptor inhibitor or at least one lily of the valley olfactory receptor inhibitor selected from the group consisting of (−)-(1R,4R,6S,10S)-4,12,12-trimethyl-9-methylene-5-oxatricyclo[8.2.0.0$^{4,6}$]dodecane, trimethyl-13-oxabicyclo[10.1.0]-trideca-4,8-diene, (+−)-ethyl 3-methyl-2-oxopentanoate and 7-propyl-2H,4H-1,5-benzodioxepin-3-one in an amount o below an amount effective to decrease the potency and/or efficacy for the at least one lily of the valley compound for a lily of the valley olfactory receptor in a subject.

In some aspects, the perfumed consumer product comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

As used herein, the term "perfumery carrier" refers to a material which is practically neutral from a perfumery point of view, i.e. which does not significantly alter the organoleptic properties of perfuming ingredients. The perfumery carrier may be a liquid or a solid.

Non-limiting examples of liquid perfumery carriers include an emulsifying system, i.e. a solvent and a surfactant system, or a solvent commonly used in perfumery. A detailed description of the nature and type of solvents commonly used in perfumery cannot be exhaustive. However, non-limiting examples solvents include dipropyleneglycol, diethyl phthalate, isopropyl myristate, benzyl benzoate, 2-(2-ethoxyethoxy)-1-ethanol or ethyl citrate. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Non-limiting examples of solid perfumery carriers include absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

As used herein, the term "perfumery base" refers a composition comprising at least one perfuming co-ingredient. A perfuming co-ingredient does not include at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof. As used herein, the term "perfuming co-ingredient" refers to compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds.

As used herein, the term "perfumery adjuvant" refers to an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Accordingly, in some aspects, the present disclosure provides a perfumed consumer product comprising an effective amount of at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof. In some aspects, the perfumed consumer product is selected from the group consisting of: air care products, home care products and laundry care products.

In some aspects, the perfumed consumer product comprising an effective amount of at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

It should be appreciated by those skilled in the art that the conception and the specific embodiments disclosed might be readily utilized as a basis for modifying or formulating other formulations for carrying the same purposes of the present invention. It should also be realized by those skilled in the art that such equivalent formulations do not depart from the spirit and scope of the disclosure as set forth herein.

The proportions in which the at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof can be incorporated into the various aforementioned products or compositions vary within a wide range of values. These values are dependent on the nature of the consumer product and on the desired organoleptic effect as well as the nature of the co-ingredients in a given composition when the at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof are mixed with other ingredients, solvents or additives commonly used in the art.

In general, for example, in the case of perfuming compositions, typical concentrations are in the order of 0.001% to 5% by weight, or even more, of at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal;

(E)-non-2-enal; and combinations thereof based on the weight of the composition into which they are incorporated. Concentrations lower than these, such as in the order of 0.01% to 100% by weight, can be used when the compositions described herein are incorporated into consumer products, the percentage being relative to the weight of the consumer product.

It should be appreciated by those skilled in the art that the conception and the specific embodiments disclosed might be readily utilized as a basis for modifying or formulating other formulations for carrying the same purposes of the present invention. It should also be realized by those skilled in the art that such equivalent formulations do not depart from the spirit and scope of the disclosure as set forth herein.

Non-limiting examples of suitable perfuming consumer product include:
- a perfume, such as a fine perfume, an Eau de Toilette, a cologne or an after-shave lotion;
- a fabric care product, such as a liquid detergent, a powder detergent, detergent tablets, a detergent bar, a detergent paste, a detergent pouch, a liquid fabric softener, fabric softener sheets, a fabric scent booster, a laundry pre-treatment, a fabric refresher, an ironing water, a laundry bleach, a carpet powder or a carpet cleaner;
- a hair care product, such as a shampoo, a hair conditioner, a hair cream, a hair oil, a hair styling product (such as a spray, mousse or gel), a hair coloration product or a hair permanent wave product;
- a skin care product, such as a face cream, a face lotion, a shaving product (such as a foam, cream, gel or oil), a body and/or hand product (such as a lotion, cream, gel or oil), a skin firming product, a depilatory, a talcum powder, a foot care cream or lotion, baby wipes, cleansing wipes, moisturizer wipes, a sun-protection product (such as a spray, lotion, cream or oil), an after-sun lotion, or a self-tanning product;
- a body deodorant or antiperspirant product, such as a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream;
- a skin-cleansing product, such as a soap bar, a shower gel, a liquid hand soap, a bath foam or an intimate wash product;
- an air freshening product, such as an air freshener spray, a gel air freshener, a liquid-wick air freshener, a solid air freshener comprising a porous substrate (such as a paper or card blotter, a porous ceramic, or a porous plastic), a liquid or gel air freshener comprising a permeable membrane, an electrically operated air freshener, and a dual purpose air freshener/disinfectant spray; and/or
- a surface care product, such as an all-purpose cleaner, a furniture polish, a wood floor cleaner, a window cleaner, a hand dishwashing product (such as a liquid, gel or paste), a machine dishwashing product (such as a powder, liquid, gel, tablet or sachet), a toilet bowl cleaning liquid, an in-cistern toilet cleaner, a toilet rim block, or a toilet rim liquid; a pet-litter.

In some aspects, the composition as defined in any of the above aspect may be absorbed on a porous or non-porous substrate in loose powder or compacted form, the substrate being selected from cellulose (paper/cardboard), vermiculite, other industrial absorbents, perlite, calcium carbonate, pumice, wood, sawdust, ground corn cob, ground rice hull, rice hull ash, biochars, starches, modified starches and mixtures thereof.

In some aspects, the consumer product is selected from the group consisting of: a fine perfume, a splash or eau de perfume, a cologne, an shave or after-shave lotion, a liquid or solid detergent, a fabric softener, a fabric refresher, an ironing water, a paper, a bleach, a carpet cleaners, curtain-care products a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, and a car care product.

The present invention is best illustrated but is not limited to the following examples.

EXAMPLES

Example 1: Identification of Putative OR10J5 Activity Enhancers

Olfactory receptor OR10J5 is a human olfactory receptor whose floral muguet compound-induced activity correlates with the sensory outcome of perception of a floral, lily of the valley, hydroxycitronellal odor note, and an overall olfactive character reminding strongly of the one of the very well-known ingredient 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof (sold under the tradename LYRAL®, hereinafter referred to as "LYRAL®".

The OR10J5 olfactory receptor is activated by floral muguet compounds. A floral muguet compound refers to certain compounds that impart a lily of the valley-like or muguet floral note, including but not limited to a lyral compound. A lyral compound may comprise LYRAL® and/or may comprise a compound such as 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof, which may be sold under the following tradenames: LYRAL®, KOVANOL®, MUGONAL®, and LANDOLAL®.

Examples of floral muguet compounds include, but are not limited to the compounds disclosed in International Patent Application Publication Nos. WO2017/009175 A1, or WO2010/091969 A1, or WO2011/029743 A1, or WO2018/134221 A1.

A dose response curve showing the activation of OR10J5 in response to the floral muguet compound 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof (sold under the tradename LYRAL®, hereinafter referred to as "LYRAL®") is shown in FIG. 1. Using a cell-based assay, OR10J5 activity was tested in a HEK293T cell line wherein the endogenous chaperone RTP1 gene has been activated and the odorant receptor chaperone was expressed according to the methods disclosed in International Patent Application Publication No. WO2016/201153 A1. The Flag-Rho-tagged receptor was co-transfected with the olfactory canonical G-protein $G_{olf}$ and was exposed to a binary mixture of a single concentration of LYRAL® and a test compound.

A library of volatile compounds was used to create binary mixtures of each compound with LYRAL® at approximately $EC_{20}$, a concentration eliciting only approximately 20% of full activity level of OR10J5 by itself. An activation cell-based assay was used for the initial enhancer candidate identification as disclosed in WO2019122236. Single binary mixture-induced receptor activity was detected by measuring the cAMP increase in the cytosol using an HTRF (Homogenous Time-Resolved Fluorescence unit) based kit (CisBio, cAMP dynamic 2 kit, 62AM4PEJ).

Figure 2:
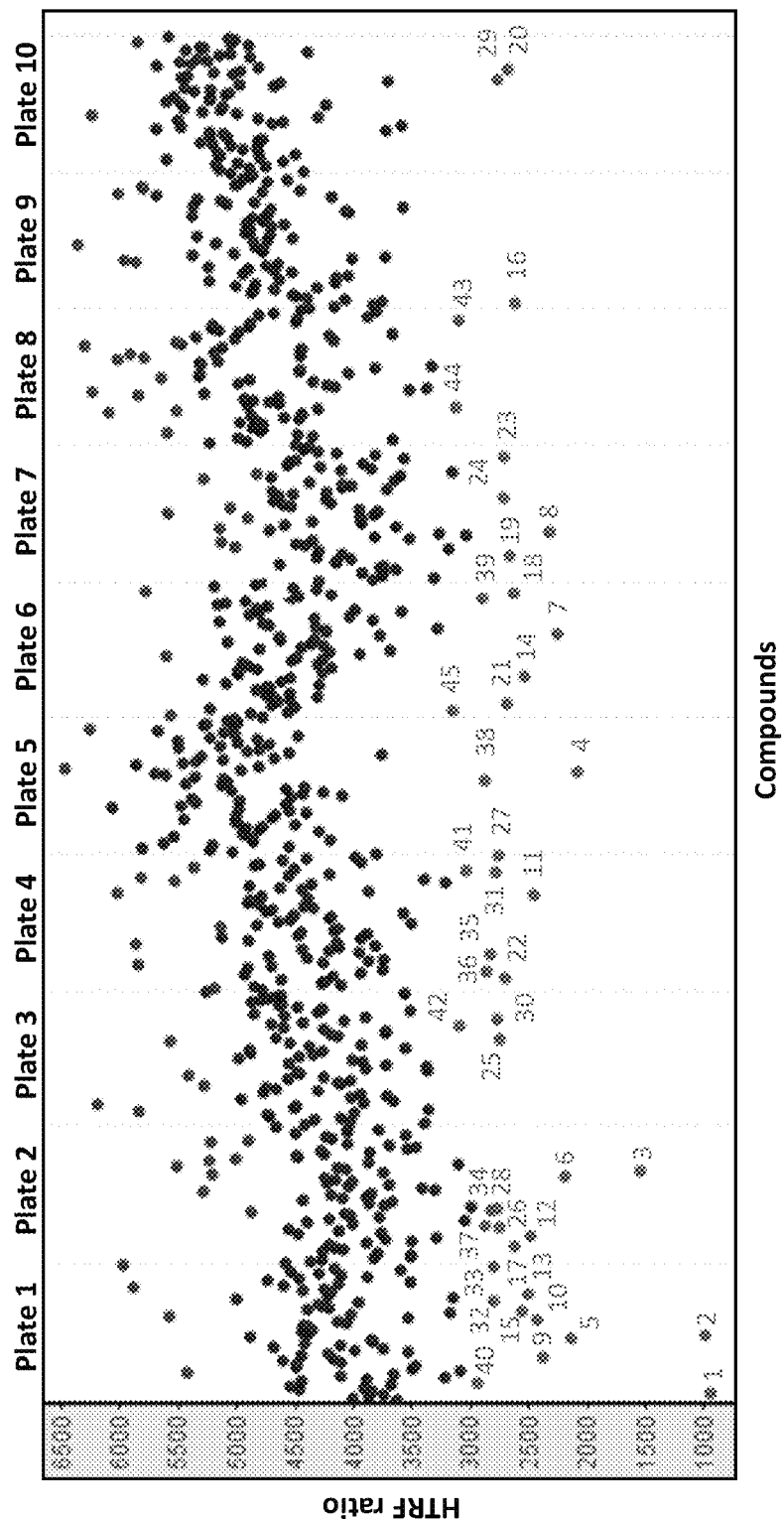
FIG. 2 shows the result of a single point binary mixture of LYRAL® and perfumery raw materials screening for OR10J5 LYRAL®-induced activity modulation (enhancement and inhibition).

800 binary mixtures were created by mixing a LYRAL® stock solution with a stock solution of each test compound to a final concentration 4.6 and 300 µM, respectively. Stock solutions were made of compounds dissolved in pure DMSO. Each mixture was presented to a cell line expressing the OR10J5 olfactory receptor. The final concentration of DMSO in each binary mixture was 0.1%, and had no visible effect on the cells (see FIG. 2).

The resulting activation was then measured and compared to LYRAL® alone (defining the baseline of the enhancement assay). The quality of the HTS process was determined and the window variability and signal reliability were assessed by calculating the Z' value of each plate. 45 hits were obtained, eight of which were OR10J5 olfactory receptor agonists (hit no. 1, 2, 5, 6, 10, 15, 25 and 34), see Table 2. These OR10J5 olfactory receptor agonists further confirmed that the dynamic range of the assay window was sufficient (as the responses recorded were well above baseline) and thus likely sensitive enough to detect even low levels of putative enhancement.

The 37 candidates remaining in Table 2 were identified and were tested in two parallel dose-response experiments to confirm the true enhancement properties of the potential candidates. First, a dose-response of each individual candidate was performed to determine if it was an agonist by itself. Second, the same candidate dose-response curve in the presence of $EC_{20}$ LYRAL® concentration (generating 20% activity on OR10J5) was assessed for activity level increase. Molecules that increased the response of the OR10J5 olfactory receptor to LYRAL® beyond $EC_{20}$, but did not display measurable intrinsic activity themselves were considered to be true enhancers and were selected for further studies. From this analysis, 20 molecules were identified that showed enhancement properties. See Table 1.

TABLE 1

Compounds confirmed as true enhancers of OR10J5 lyral activation.

| | | | | | | | |
|---|---|---|---|---|---|---|---|
| 1. | Octanal | 2. | (E)-Dec-2-enal | 3. | 2-Phenylpropanal | 4. | (E)-But-2-enal |
| 5. | 3-Methylbenzaldehyde | 6. | 3-(1,3-Benzodioxol-5-yl)-2-methylpropanal | 7. | (+−)-3-(4-Methyl-3-penten-1-yl)-3-cyclohexene-1-carbaldehyde + (+−)-4-(4-Methyl-3-penten-1-yl)-3-cyclohexene-1-carbaldehyde | 8. | Heptanal |
| 9. | 4-Propan-2-ylbenzaldehyde | 10. | (3R)-3,7-Dimethyloct-6-enal | 11. | (+)-(3S)-3-[(1R)-4-Methyl-3-cyclohexen-1-yl]butanal + (+)-(3R)-3-[(1R)-4-Methyl-3-cyclohexen-1-yl]butanal | 12. | Hexanal |
| 13. | 2,6-Dimethylhept-5-enal | 14. | Benzaldehyde | 15. | 2-Methyl-3-(4-methylphenyl)propanal | 16. | 3,5,6-Trimethyl-3-Cyclohexene-1-Carbaldehyde + 2,4,6-Trimethyl-3-Cyclohexene-1-Carbaldehyde |
| 17. | 2,4,6-Trimethylcyclohex-3-ene-1-carbaldehyde | 18. | 4-Ethylbenzaldehyde | 19. | 6-Methoxy-2,6-dimethylheptanal | 20. | (E)-Non-2-enal |

TABLE 2

Compounds selected from the enhancement screen, numbered by decreasing OR10J5 activity (span).

| | | | | | | | |
|---|---|---|---|---|---|---|---|
| 1. | methyl 2-({-[3 or 4-(4-hydroxy-4-methylpentyl)-3-cyclohexen-1-ylidene]methyl}amino)benzoate | 2. | Lyral | 3. | Octanal | 4. | 2-Decenal |
| 5. | (+−)-7-hydroxy-3,7-dimethyloctanal | 6. | (+−)-2,5-dimethyl-2-indanmethanol | 7. | 2-phenylpropanal | 8. | E-2-butenal |
| 9. | m-Tolualdehyde | 10. | (+−)-Tetrahydro-2-isobutyl-4-methyl-4(2H)-pyranol | 11. | 3-(1,3-benzodioxol-5-yl)-2-methylpropanal | 12. | (+−)-3-(4-methyl-3-penten-1-yl)-3-cyclohexene-1-carbaldehyde + (+−)-4-(4-methyl-3-penten-1-yl)-3-cyclohexene-1-carbaldehyde |
| 13. | 4-hydroxy-3,5-dimethoxybenzaldehyde | 14. | (+−)-2,6,10-trimethyl-9-undecenal | 15. | Methyl n-benzylideneanthranilate | 16. | Heptanal |
| 17. | 4-(2-propanyl)benzaldehyde | 18. | (+)-(R)-3,7-dimethyl-6-octenal | 19. | Methyloctylacetaldehyde | 20. | 3-(4-methylcyclohex-3-en-1-yl)butanal |
| 21. | Zantryle | 22. | Lemongrass Oil | 23. | Cis-Nonenal | 24. | Adehyde C6 |
| 25. | (+−)-7-hydroxy-3,7-dimethyloctanal | 26. | (+−)-1-methyl-4-(4-methyl-3-pentenyl)-3-cyclohexene-1-carbaldehyde | 27. | (+−)-2,6-dimethyl-5-heptenal | 28. | Benzaldehyde |
| 29. | 9-decenal | 30. | (2Z)-3,7-dimethyl-2,6-octadienal & (2E)-3,7-dimethyl-2,6-octadienal | 31. | Citronella Oil Java | 32. | (E,E)-2,4-Decadienal |

TABLE 2-continued

Compounds selected from the enhancement screen, numbered by decreasing OR10J5 activity (span).

| | | | |
|---|---|---|---|
| 33. Nonanal | 34. 2-methyl-6-methylideneoctan-2-ol | 35. Undecalactone Delta | 36. (+−)-2-methyl-3-(4-methylphenyl)propanal |
| 37. Benzo[d][1,3]dioxole-5-carbaldehyde | 38. 3,5,6-trimethyl-3-cyclohexene-1-carbaldehyde + 2,4,6-trimethyl-3-cyclohexene-1-carbaldehyde | 39. 2,4,6-trimethyl-3-cyclohexene-1-carbaldehyde | 40. 2-ethyl-3-hydroxy-4(4H)-pyranone |
| 41. 4-ethylbenzaldehyde | 42. (3S,3aS,6R,7aR)-3,6-dimethylhexahydro-1-benzofuran-2(3H)-one | 43. (+−)-6-methoxy-2,6-dimethylheptanal | 44. Nonylenic Aldehyde |
| 45. (+−)-8,8-dimethyl-1,2,3,4,5,6,7,8-octahydro-2-naphthalenecarbaldehyde + (+−)-5,5-dimethyl-1,2,3,4,5,6,7,8-octahydro-2-naphthalenecarbaldehyde + (+−)-2,2-dimethyltricyclo[6.2.1.0$^{1,6}$]undecan-7-one | | | |

Example 2: Characterization of OR10J5 Activity Enhancement Specificity

LYRAL® enhancement specificity was tested on compounds that were structurally similar to enhancers identified. Dose response curves to LYRAL® were obtained in the presence of a steady concentration of a test compound and compared to a dose-response curve of LYRAL® alone. The resulting enhancement was quantified by means of $EC_{50}$-fold shift (potency increase) and the efficacy span ratio (efficacy increase).

The $EC_{50}$-fold shift was obtained by dividing the $EC_{50}$ of LYRAL®+compound by the reference $EC_{50}$ of LYRAL® alone. The span ratio was obtained by dividing the span of LYRAL®+compound by the reference span of LYRAL® alone.

Figure 3:
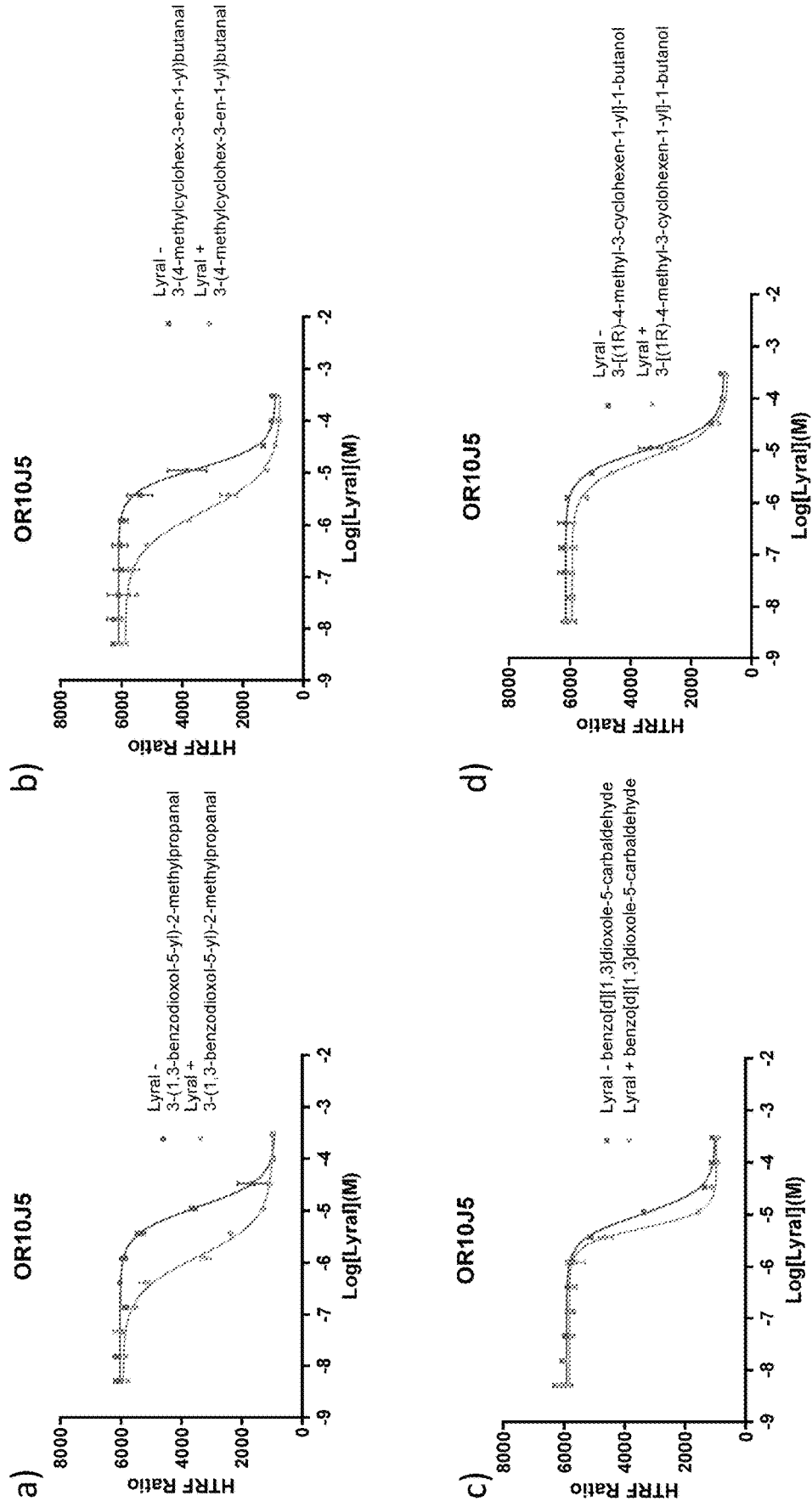
FIG. 3 shows the distinct enhancement levels obtained on OR10J5 LYRAL®-induced activation with a) 3-(1,3-benzodioxol-5-yl)-2-methylpropanal, b) 3-(4-methylcyclohex-3-en-1-yl)butanal, c) benzo[d][1,3]dioxole-5-carbaldehyde and d) 3-[(1R)-4-methyl-3-cyclohexen-1-yl]-1-butanol, and the absence of enhancement for the latter two compounds.

FIG. 3 shows the distinct enhancement levels obtained with a) 3-(1,3-benzodioxol-5-yl)-2-methylpropanal and b) 3-(4-methylcyclohex-3-en-1-yl)butanal, and the absence of enhancement with c) benzo[d][1,3]dioxole-5-carbaldehyde and d) 3-[(1R)-4-methyl-3-cyclohexen-1-yl]-1-butanol for OR10J5. OR10J5 activation by LYRAL® was specifically enhanced by 3-(1,3-benzodioxol-5-yl)-2-methylpropanal and 3-(4-methylcyclohex-3-en-1-yl)butanal, but not by structurally related compounds as indicated by the corresponding fold shifts: a 9.2 and 6.7 fold shift for 3-(1,3-benzodioxol-5-yl)-2-methylpropanal and 3-(4-methylcyclohex-3-en-1-yl)butanal respectively, versus a 1.8 and 1.3 fold shift for benzo[d][1,3]dioxole-5-carbaldehyde and 3-[(1R)-4-methyl-3-cyclohexen-1-yl]-1-butanol, respectively.

Figure 4:
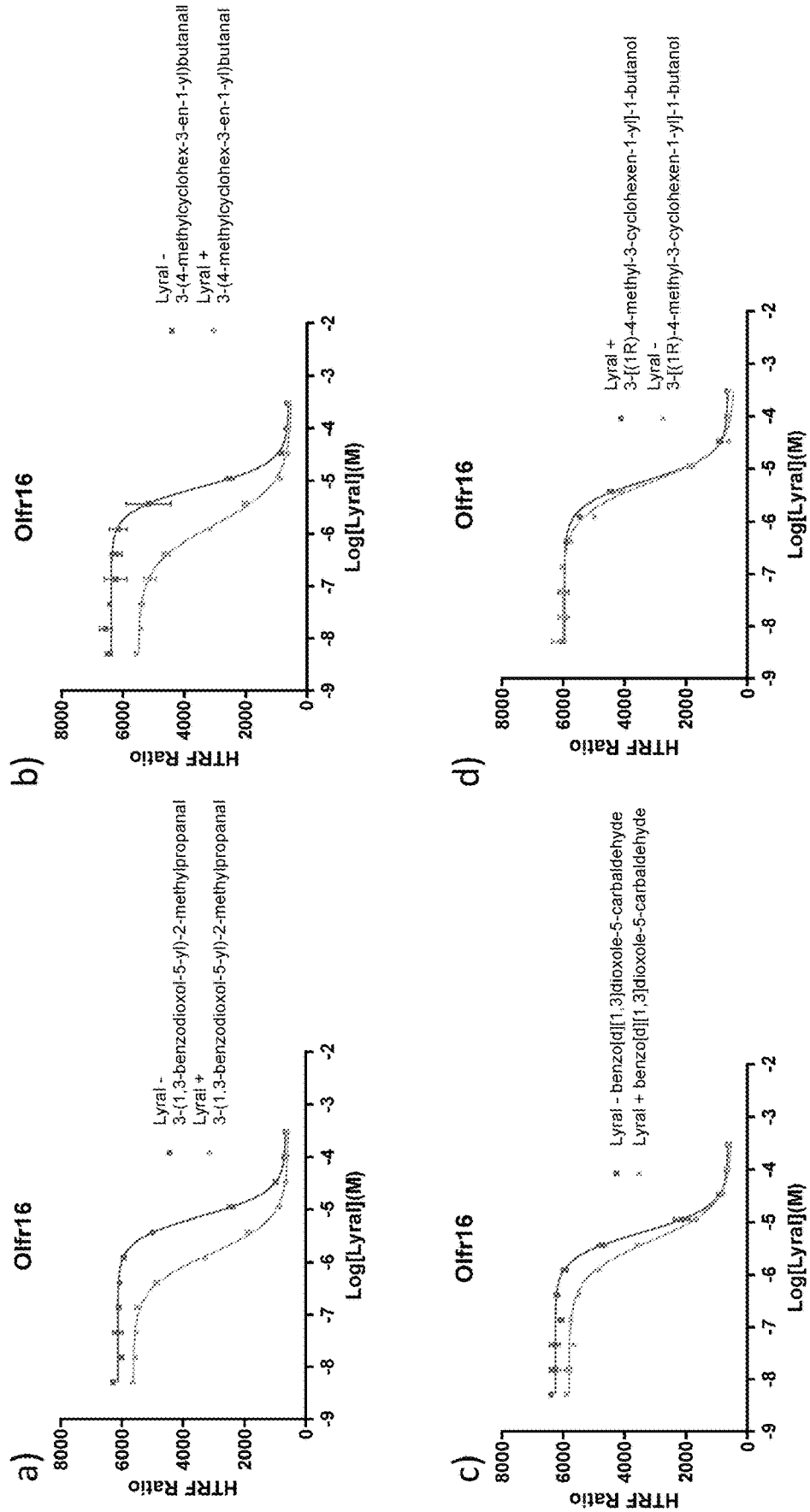
FIG. 4 shows the distinct enhancement levels obtained on Olfr16 LYRAL®-induced activation with a) 3-(1,3-benzodioxol-5-yl)-2-methylpropanal, b) 3-(4-methylcyclohex-3-en-1-yl)butanal, c) benzo[d][1,3]dioxole-5-carbaldehyde and d) 3-[(1R)-4-methyl-3-cyclohexen-1-yl]-1-butanol, and the absence of enhancement for the latter two compounds.

FIG. 4 shows the distinct enhancement levels obtained with 3-(1,3-benzodioxol-5-yl)-2-methylpropanal and 3-(4-methylcyclohex-3-en-1-yl)butanal, and the absence of enhancement with benzo[d][1,3]dioxole-5-carbaldehyde and 3-[(1R)-4-methyl-3-cyclohexen-1-yl]-1-butanol for the mouse ortholog of OR10J5, Olfr16. Olfr16 activation by LYRAL® was specifically enhanced by 3-(1,3-benzodioxol-5-yl)-2-methylpropanal and 3-(4-methylcyclohex-3-en-1-yl)butanal, but not by structurally related compounds as indicated by the corresponding fold shifts: a 5 fold shift for both 3-(1,3-benzodioxol-5-yl)-2-methylpropanal and 3-(4-methylcyclohex-3-en-1-yl)butanal, versus a 1.5 and 1.1 fold shift for benzo[d][1,3]dioxole-5-carbaldehyde and (3S)-3-[(1R)-4-methyl-3-cyclohexen-1-yl]-1-butanol, respectively. These results indicate enhancement of other mammalian olfactory receptors.

Figure 5:
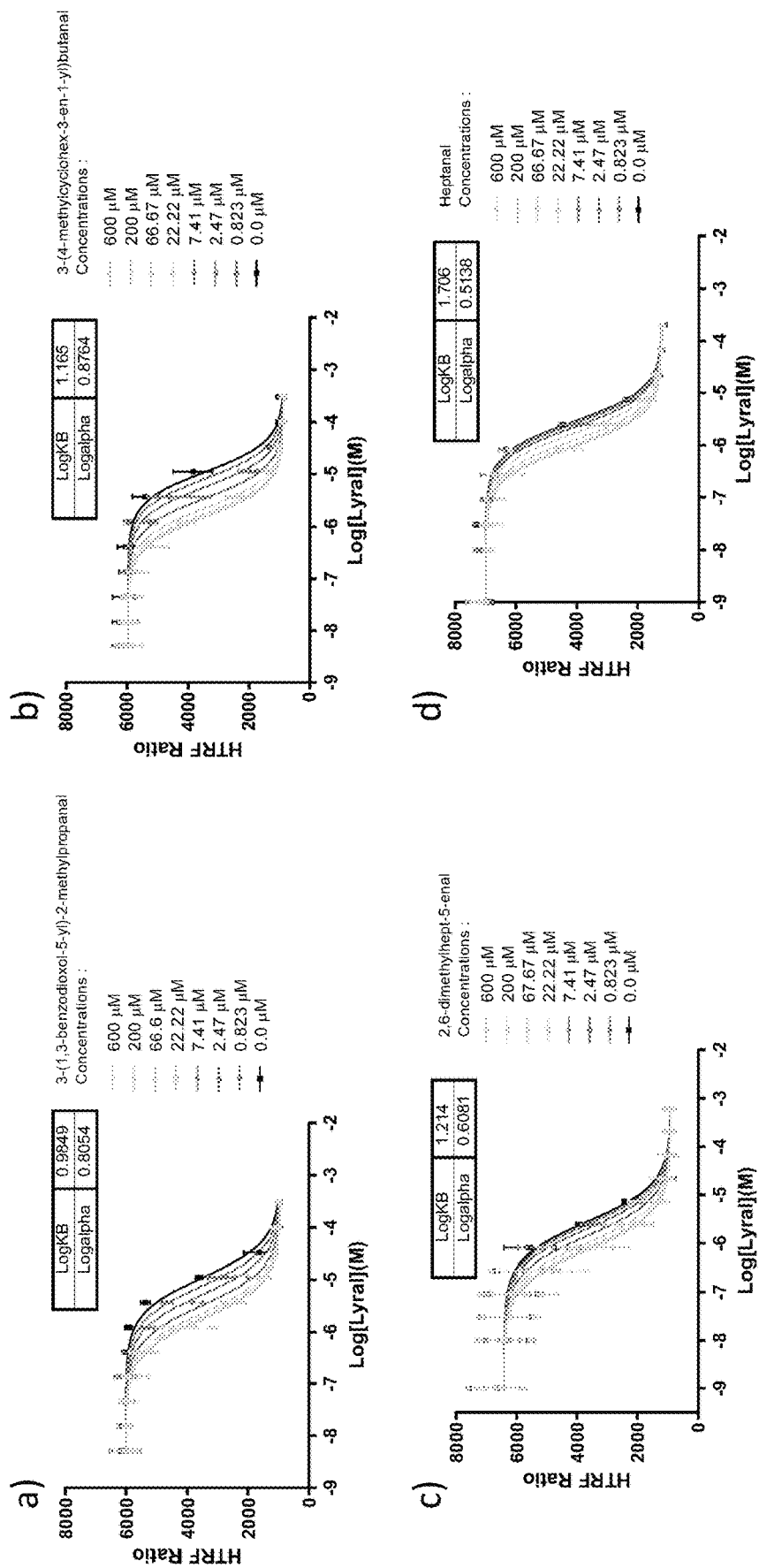
FIG. 5 displays a series of dose response curves of OR10J5 activation in response to LYRAL® in the presence of serial concentrations of a) 3-(1,3-benzodioxol-5-yl)-2-methylpropanal, b) 3-(4-methylcyclohex-3-en-1-yl)butanal, c) 2,6-dimethylhept-5-enal and d) heptanal, and also indicates the corresponding calculated log values for the cooperativity factor α and the equilibrium constant $K_B$.

Example 3: LYRAL® Enhancers Act as Positive Allosteric Modulators (PAM) to Enhance OR10J5 Olfactory Receptor Activity Functional dose-response experiments were performed to reveal the allosteric nature of the interaction between 3-(1,3-benzodioxol-5-yl)-2-methylpropanal, 3-(4-methylcyclohex-3-en-1-yl)butanal, 2,6-dimethylhept-5-enal and heptanal and OR10J5. The level of enhancement of OR10J5's activation was evaluated at distinct concentrations of each enhancer. Using the same cell-based assay described earlier, dose response curves of OR10J5 to LYRAL® in the presence of serial concentrations of the enhancers spanning from 0 to 600 μM were performed, see FIG. 5. The curves were obtained by applying the simplified Allosteric EC50 shift effect equation (available in Prism7) derived from the ternary complex interaction model. The enhancement levels recorded were not linearly dependent on the concentration of the enhancer, and the following key parameters values for $\alpha$ (the cooperativity factor) and $K_B$ (the equilibrium dissociation constant of the enhancer) were obtained from the model for each enhancer: 3-(1,3-benzodioxol-5-yl)-2-methylpropanal, $\alpha=6.3$ and $K_B=10$ μM; 3-(4-methylcyclohex-3-en-1-yl)butanal, $\alpha=7.5$ and $K_B=15$ μM; 2,6-dimethylhept-5-enal, $\alpha=4.1$ and $K_B=16$ μM; and heptanal; $\alpha=3.2$ and $K_B=51$ μM. $\alpha>1$ is indicative of positive allosteric modulation.

Example 4: Human Sensitivity to LYRAL® is Increased in the Presence of an Enhancer Sensitivity of human individuals to LYRAL® was evaluated by performing an odor detection threshold (ODT) test. The ODT test consisted of identifying the concentration for which 50%, preferably 66%, of the panelists are able to determine which of three containers contains the target compound LYRAL® in a series of forced-choice triangle tests. Two tests were performed to calculate the ODT in mixtures containing LYRAL® plus a perceivable background odor of chemically similar molecules a) the enhancer, 3-(4-methylcyclohex-3-en-1-yl)butanal and b) the non-enhancing volatile compound, 3-[(1R)-4-methyl-3-cyclohexen-1-yl]-1-butanol. These two molecules are chemically similar. The perceived intensity of the two background odors was monitored to be isointense to control that the responses recorded answer were intensity independent.

Figure 6:
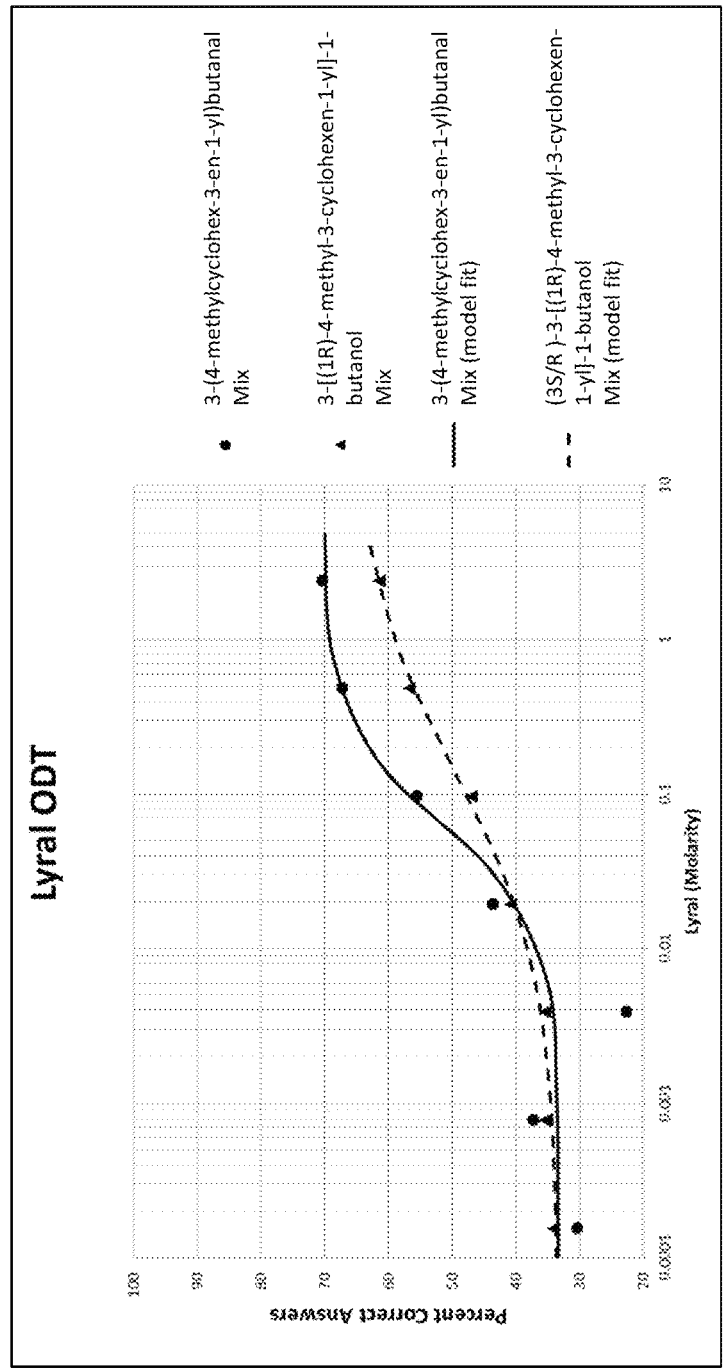
FIG. 6 shows human panelists more sensitive to LYRAL® in the presence of an enhancer compared to a non-enhancing compound.

28 panelists were given a series of triangle tests with increasing concentrations of LYRAL® in the presence of 3-(4-methylcyclohex-3-en-1-yl)butanal at a concentration of 0.1%. Within each triangle test, the three samples contained 3-(4-methylcyclohex-3-en-1-yl)butanal at 0.1% and one sample also contained LYRAL®. 28 panelists were given a series of triangle tests with increasing concentration of Lyral® in the presence of 3-[(1R)-4-methyl-3-cyclohexen-1-yl]-1-butanol at a concentration of 7%. Within each triangle test, the three samples contained 3-[(1R)-4-methyl-3-cyclohexen-1-yl]-1-butanol at 7% and one sample also contained LYRAL®. In each triangle test, the panelists were asked to identify the one sample that was different from the other two samples. Corresponding results are shown in FIG. 6.

Figure 7:
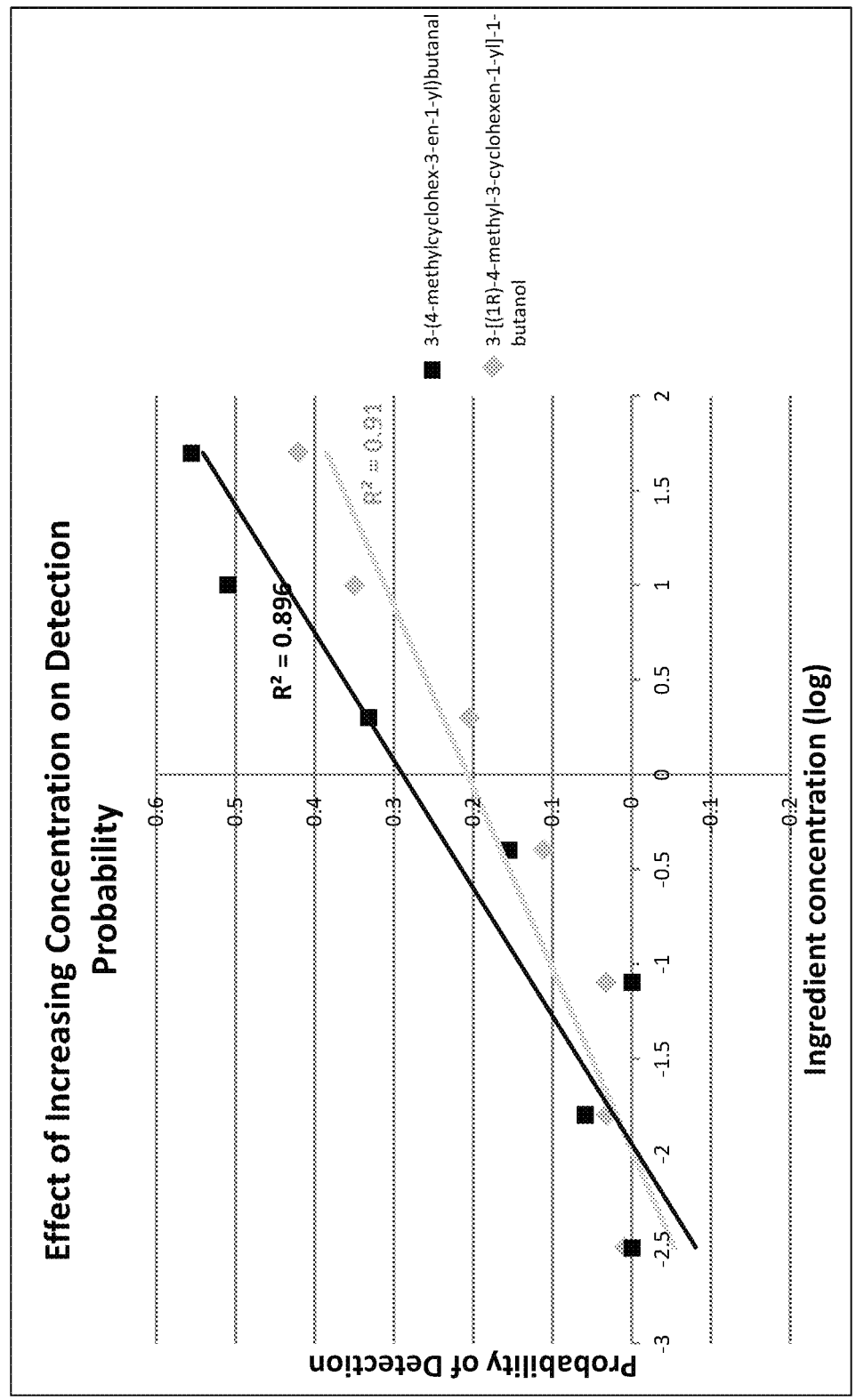
FIG. 7 shows proportion of correct LYRAL® detection responses increased at a higher rate when LYRAL® was mixed with the enhancer versus neutral compound as concentration increased.

The proportion of correct responses was adjusted to account for the probability of guessing using Abbott's formula frequently used in the field (Lawless, 2010). A linear regression, with Material (Enhancer versus Neutral compound) and log-transformed Concentration Level as explanatory variables, and proportion of correct responses as a response variable, yielded a significant main effect of Material (p=0.03) and a marginally significant interaction (p=0.052), indicating that with increasing concentration, proportion of correct responses increased at a higher rate when LYRAL® was mixed with the enhancer (versus mixed with the neutral compound. See FIG. 7).

Example 5: OR10J5 Activity Enhancement is Independent of OR10J5 Agonists

OR10J5 activity enhancement was tested with an additional agonist and with one of the test compounds and conditions described in the Examples above. Dose response curves to (+−)-2,5-dimethyl-2-indanmethanol was obtained in the presence of a steady concentration of the test compound and compared to a dose-response curve of the agonist alone. The resulting enhancement was quantified by means of $EC_{50}$-fold shift (potency increase) and the efficacy span ratio (efficacy increase) as described above.

Figure 8:
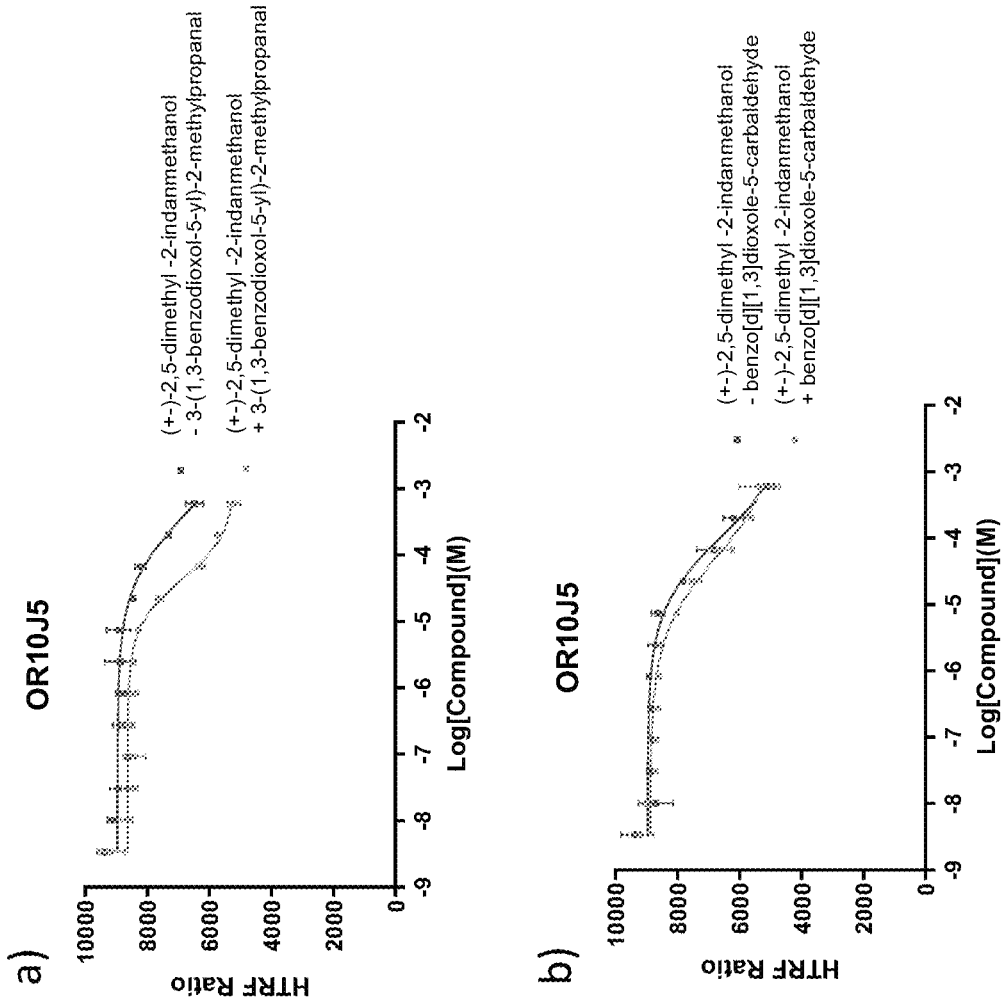
FIG. 8 shows the distinct enhancement levels obtained on OR10J5 (+−)-2,5-dimethyl-2-indanmethanol-induced activation with a) 3-(1,3-benzodioxol-5-yl)-2-methylpropanal, and b) benzo[d][1,3]dioxole-5-carbaldehyde, and the absence of enhancement for the latter compound.

FIG. 8 shows the distinct enhancement levels obtained with a) 3-(1,3-benzodioxol-5-yl)-2-methylpropanal, and the absence of enhancement with b) benzo[d][1,3]dioxole-5-carbaldehyde OR10J5 activation by (+−)-2,5-dimethyl-2-indanmethanol was specifically enhanced by 3-(1,3-benzodioxol-5-yl)-2-methylpropanal, but not by the structurally related compound as indicated by the corresponding fold shifts: a 8.6 and 2.0 fold shift for 3-(1,3-benzodioxol-5-yl)-2-methylpropanal and benzo[d][1,3]dioxole-5-carbaldehyde, respectively.

This demonstrates that the test compound is specifically enhancing the activity of OR10J5 independently of the nature of the agonist (activating compound). In this particular case (+−)-2,5-dimethyl-2-indanmethanol, is a partial agonist of OR10J5 and yet was enhanced by 3-(1,3-benzodioxol-5-yl)-2-methylpropanal which led to a 1.7 fold efficacy increase within the dynamic range of the dose response in addition to the potency increase (see FIG. 8a). This further indicated that the enhancement was mediated through a receptor binding event and not likely mediated by receptor-independent effects such as on the assay cells themselves.

Example 6: OR10J5 Activity Inhibitors Identification

Using the same cell-based assay described herein, OR10J5 activity inhibition was tested with binary mixtures of LYRAL® and a test compound. Volatile compounds were used to create binary mixtures of each compound with LYRAL® at approximately $EC_{80}$, a concentration eliciting approximately 80% of full activity level of OR10J5 by itself. An activation cell-based assay was used for the initial inhibitor candidate identification as disclosed in WO2019101813. Single binary mixture-induced receptor activity was detected by measuring the cAMP increase in the cytosol using the same HTRF-based kit described in Example 1.

The binary mixtures were created by mixing a LYRAL® stock solution with a stock solution of each test compound to a final concentration XXX and 300 µM, respectively. Stock solutions were made of compounds dissolved in pure DMSO. Each mixture was presented to a cell line expressing the OR10J5 olfactory receptor. Similar to the enhancement screening conditions, the final concentration of DMSO in each binary mixture was 0.1%, and had no visible effect on the cells. The resulting activation was measured and compared to LYRAL® alone (defining the activity baseline of the assay, ~$EC_{80}$). If a given binary mixture exhibited a decreased activity compared to LYRAL® alone, the corresponding compound was considered a candidate inhibitor. The quality of the HTS process was determined and the window (activity range between $EC_{80}$ and the DMSO baseline) variability and signal reliability were assessed by calculating the Z' value of each plate.

Candidate inhibitors identified were tested in a dose-response inhibition experiments to confirm the inhibition properties of the potential candidates. The dose-response curve in the presence of $EC_{80}$ LYRAL® concentration (generating 80% activity on OR10J5) was assessed for dose-dependent activity level decrease. FIG. 9 shows 4 molecules, (−)-(1R,4R,6S,10S)-4,12,12-trimethyl-9-methylene-5-oxatricyclo[8.2.0.0$^{4,6}$]dodecane, trimethyl-13-oxabicyclo-[10.1.0]-trideca-4,8-diene, (+−)-ethyl 3-methyl-2-oxopentanoate, 7-propyl-2H,4H-1,5-benzodioxepin-3-one that decreased the response of the OR10J5 olfactory receptor to LYRAL®. Both potency and efficacy of the confirmed inhibitors were evaluated by calculating their half-maximal inhibition concentration ($IC_{50}$) relative to $EC_{80}$ LYRAL and the amount of inhibition (Span), respectively. The $IC_{50}$ values indicate the inhibition level with respect to the potency. The Span values indicate the inhibition level with respect to the inhibition efficacy. The $IC_{50}$ values are used to rank order the compounds from strongest to weakest inhibitors of OR10J5 (FIG. 9a-d).

Volatiles compounds used in perfumery creations such as the ones shown in FIG. 9 may have inhibitory properties in addition to their own organoleptic qualities that can be detrimental to the perception of a desired olfactory quality. Their use in such a fragrance can be avoided or limited during the creation process, resulting in a greater perception of the desired quality.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method,
   wherein the method conveys, enhances, improves or modifies an intensity and/or sensitivity of the perception of a floral muguet odor in a subject, wherein the method comprises contacting the subject with at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (±)-3-(4-methyl-3-penten-1-yl)-3-cyclohexene-1-carbaldehyde, (±)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof, wherein the subject is contacted with the at least one positive allosteric modulator in an amount sufficient to convey, enhance, improve or modify the intensity and/or sensitivity of the perception of the floral muguet odor in the subject.

2. The method of claim 1, wherein the method further comprises contacting the subject with at least one floral muguet compound.

3. The method of claim 1, wherein the at least one positive allosteric modulator is incorporated into a perfuming composition.

4. The method of claim 3, wherein the perfuming composition further comprises at least one floral muguet compound.

5. The method of claim 4, wherein the at least one floral muguet compound is 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof.

6. The method of claim 3, wherein the perfuming composition is incorporated into a consumer product.

7. The method of claim 1, wherein the at least one positive allosteric modulator is incorporated into a consumer product.

8. The method of claim 7, wherein the consumer product further comprises at least one floral muguet compound.

9. A method, wherein the method increases the potency and/or efficacy of at least one floral muguet compound for a floral muguet olfactory receptor in a subject, wherein the method comprises contacting the subject with at least one positive allosteric modulator selected from the group consisting of: octanal; (E)-dec-2-enal, 2-phenylpropanal; (E)-but-2-enal; 3-methylbenzaldehyde; 3-(1,3-benzodioxol-5-yl)-2-methylpropanal; (±)-3-(4-methyl-3-penten-1-yl)-3-cyclohexene-1-carbaldehyde, (±)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof, wherein the subject is contacted with the at least one positive allosteric modulator in an amount sufficient to increase the potency and/or efficacy of the at least one floral muguet compound for a floral muguet olfactory receptor in the subject.

10. The method of claim 9, wherein the amount sufficient of the at least one positive allosteric modulator increases the potency and/or efficacy for the at least one floral muguet compound for a floral muguet olfactory receptor 2 fold to 30 fold.

11. The method of claim 9, wherein the increase in the potency and/or efficacy for the at least one floral muguet compound for the floral muguet olfactory receptor conveys, enhances, improves or modifies an intensity and/or sensitivity of the perception of a floral muguet odor in the subject.

12. The method of claim 9, wherein the floral muguet olfactory receptor is the OR10J5 olfactory receptor.

13. The method of claim 9, wherein the method further comprises contacting the subject with at least one floral muguet compound.

14. The method of claim 9, wherein the at least one positive allosteric modulator is incorporated into a perfuming composition.

15. The method of claim 9, wherein the at least one positive allosteric modulator is incorporated into a consumer product.

16. The method of claim 9, wherein the at least one floral muguet compound is 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof.

* * * * *